(12) United States Patent
Wu et al.

(10) Patent No.: US 9,687,658 B2
(45) Date of Patent: Jun. 27, 2017

(54) SYSTEMS AND METHODS FOR A COMMUNICATION BRIDGE BETWEEN AN IMPLANTABLE MEDICAL DEVICE AND AN EXTERNAL DEVICE

(71) Applicant: Pacesetter, Inc., Sunnyvale, CA (US)

(72) Inventors: Yonjian Wu, Saratoga, CA (US); Reza Shahandeh, Thousand Oaks, CA (US); Samir Shah, Valencia, CA (US); Chao-Wen Young, Cupertino, CA (US); Mostafa Sadeghi, Los Angeles, CA (US); Jun Yang, Valencia, CA (US); Thanh Tieu, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/676,659

(22) Filed: Apr. 1, 2015

(65) Prior Publication Data

US 2016/0287887 A1 Oct. 6, 2016

(51) Int. Cl.
*A61N 1/00* (2006.01)
*A61N 1/372* (2006.01)
(52) U.S. Cl.
CPC ..... *A61N 1/37223* (2013.01); *A61N 1/37252* (2013.01)
(58) Field of Classification Search
CPC .............................. A61N 1/37223; A61N 1/08
USPC ...................................................... 607/60, 5
See application file for complete search history.

(56) References Cited

U.S. PATENT DOCUMENTS

| 7,164,886 B2 | 1/2007 | Mowery et al. |
| 2003/0149459 A1* | 8/2003 | Von Arx .................. A61N 1/08 607/60 |
| 2005/0187593 A1* | 8/2005 | Housworth .......... A61B 5/0031 607/60 |
| 2006/0030903 A1* | 2/2006 | Seeberger .......... A61N 1/37223 607/60 |
| 2009/0035740 A1* | 2/2009 | Reed .................... G09B 23/288 434/265 |
| 2012/0057518 A1 | 3/2012 | Herrala et al. |

\* cited by examiner

*Primary Examiner* — Nadia A Mahmood
(74) *Attorney, Agent, or Firm* — Theresa A. Raymer

(57) ABSTRACT

Systems and methods are provided for bridging a bi-directional communication link between an external device and an implantable medical device (IMD). The systems and methods establish a first bi-directional communication link between an external device and a wireless bridge device according to a wireless protocol, and establish a second bi-directional communication link between the wireless bridge device and an IMD concurrently with the first bi-direction communication link according to the wireless protocol. The systems and methods further receive a data packet from the external device at the wireless bridge device. The data packet is received during the communication interval. The systems and methods further transmit the data packet from the wireless bridge device to the IMD during the communication interval.

20 Claims, 9 Drawing Sheets

SYSTEMS AND METHODS FOR A COMMUNICATION BRIDGE BETWEEN AN IMPLANTABLE MEDICAL DEVICE AND AN EXTERNAL DEVICE

BACKGROUND OF THE INVENTION

Embodiments of the present disclosure generally relate to systems and methods for a bi-directional communication link between devices, and more particularly for a communication bridge between an implantable medical device and an external device.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a microprocessor that is configured to handle RF communication with an external device as well as control patient therapy. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Recently, the IMD may communicate using commercial protocols such as Bluetooth Low Energy (BLE), which are compatible with commercial wireless devices such as tablet computers, smartphones, and the like. However, commercial protocols communicate along a 2.450 gigahertz industrial, scientific and medical (ISM) radio band which is susceptible to interference. Particularly, the communications transmitted from the IMD along the ISM band suffers due to path attenuation as the transmission propagate through the body of the patient. Thereby limiting the communication range of the IMD with the external device, for example, to less than a meter. A need exists for improved methods and systems for extending the communication range of the IMD with the external device.

BRIEF SUMMARY

In accordance with an embodiment herein, a method is provided for bridging a bi-directional communication link between an external device and an implantable medical device (IMD). The method includes establishing a first bi-directional communication link between an external device and a wireless bridge device according to a wireless protocol. The method further includes establishing a second bi-directional communication link between the wireless bridge device and an IMD concurrently with the first bi-directional communication link according to the wireless protocol. The method also includes receiving a data packet from the external device at the wireless bridge device. The data packet is received during the communication interval. The method further includes transmitting the data packet from the wireless bridge device to the IMD during the communication interval.

In an embodiment, a wireless bridge device for bridging a bi-directional communication link between an external device and an implantable medical device (IMD) is provided. The wireless bridge device includes a housing and at least one antenna. The wireless bridge device also includes a system on chip (SoC) within the housing electrically coupled to the at least one antenna. The SoC includes one or more processors and is configured to establish a first bi-directional communication link with an external device according to a wireless protocol. The SoC is also configured to establish a second bi-directional communication link with an IMD concurrently with the first bi-directional communication link according to the wireless protocol, and receive a data packet from the external device via the at least one antenna during a communication interval. The SoC is also configured to transmit the data packet to the IMD via the at least one antenna during the communication interval.

DETAILED DESCRIPTION

Figure 1:
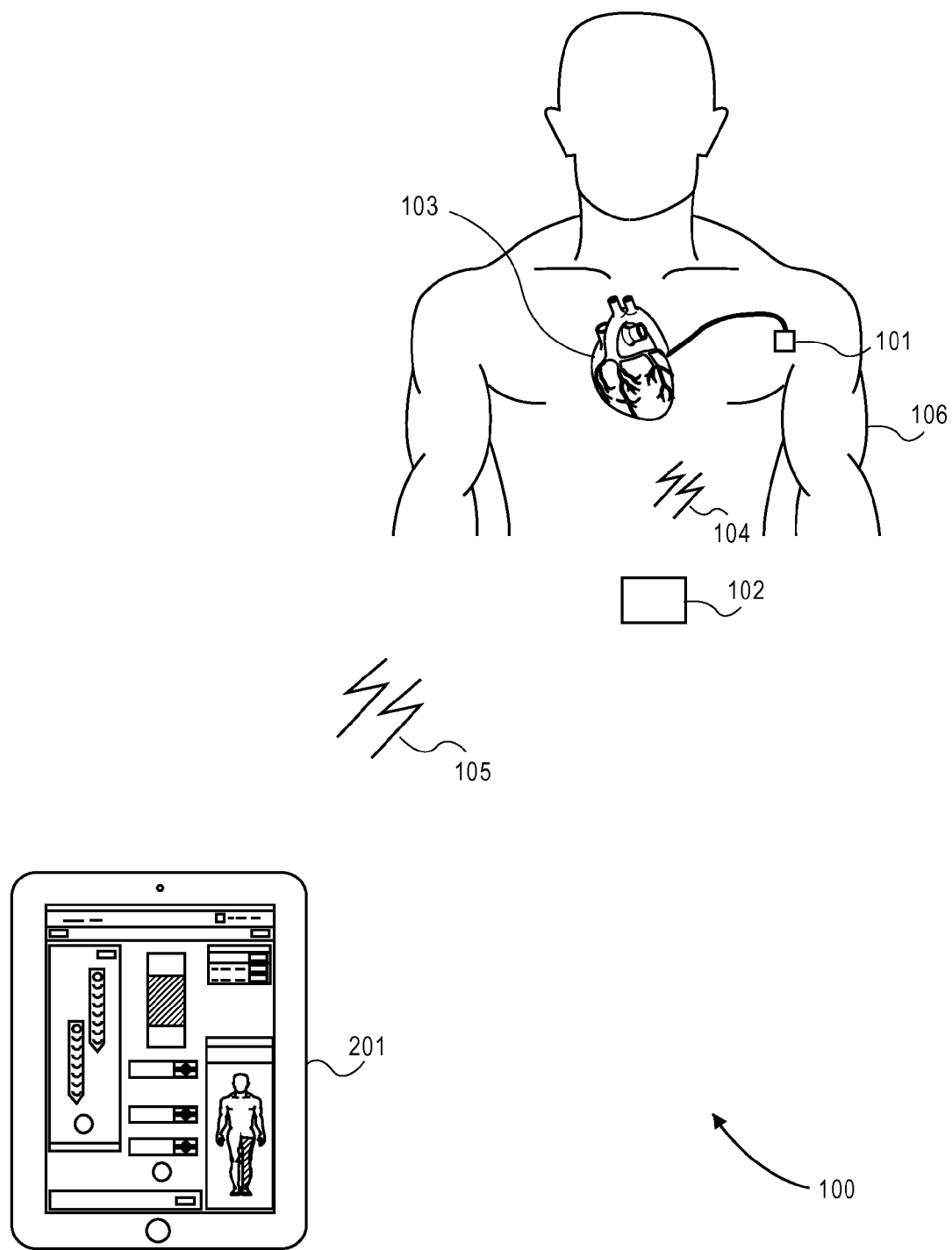
FIG. 1 illustrates simplified block diagram of a system for initiating a bi-directional communication link, according to an embodiment of the present disclosure.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system for bridging a bi-directional communication link between an external device and an implantable medical device (IMD). For example, a wireless bridge device is configured to relay wireless transmissions between the external device and the IMD. The wireless bridge device may first establish a communication link with the external device configured as a master and the wireless bridge configured as a slave. The wireless bridge device may receive connection information (e.g., serial number) corresponding to the IMD. Based on the connection information, the wireless bridge device may establish a communication link, configured as a master, with the IMD configured as a slave. Thereby, the wireless bridge may concurrently include two communication links between the external device and the IMD. When the two communication links are established, the wireless bridge device may relay or pass information (e.g., data packets) received from the first device to the second device and vice versa.

The wireless bridge device is a mobile device, which may be positioned and/or repositioned within a room and/or on a patient to change the proximity of the wireless bridge to the IMD. For example, the wireless bridge device may be repositioned closer to the IMD by positioning the IMD on a chest of a patient. The wireless bridge device may include a system on chip (SoC) solution. The SoC may include a central processing unit (CPU) core (e.g., 8051, ARM cortex) with one or more analog components (e.g., amplifiers, analog to digital converters, filters, digital to analog converters), memory (e.g., EEPROM, RAM, ROM, Flash), transceiver, and/or the like. The CPU core executes instructions stored on the memory to perform one or more applications. For example, the SoC may be configured to establish communication links with one or more other devices (e.g., the external device, the IMD) according to a wireless protocol, such as a Bluetooth Low Energy (BLE), Bluetooth, ZigBee, or the like. Additionally or alternatively, the SoC may be configured to implement security protocols (e.g., encryption algorithms, one or more message authentication codes) and/or software rules when establishing and/or transmitting data along one or more communication links.

Optionally, the SoC may be a BLE SoC configured for establishing bi-directional communication links and transmitting and/or receiving data according to the BLE protocol. The BLE protocol is defined within "Bluetooth Specification Version 4.1, published Dec. 3, 2013 (incorporated herein by reference). The BLE protocol is a master-slave protocol operating within a frequency range of 2400-2483.5 MHz (including guard bands). However, the BLE protocol uses 40 RF channels using a 2 MHz bandwidth. The 40 RF channels are allocated into two channel types, a data channel (having 37 channels) and an advertising channel (having 3 channels). The data channel is used by devices on a BLE network for communication between connected devices. The advertising channel is used by devices on the BLE network to discover new devices, initiating a connection, and broadcasting data. Each RF channel (data and advertising channel) is allocated a unique channel index, such that, if two devices wish to communicate, the transceivers of each device must be tuned to the same RF channel at the same time.

Data transmitted on the RF channels are grouped into data packets. The data packets are transmitted at 1 Mbps and include four entities, a preamble, an access address, a protocol data unit (PDU), and a cyclic redundancy check (CRC). The preamble contains 8 bits and is used by the receiver to perform frequency synchronization, symbol timing estimation, and automatic gain control training. The access address contains 32 bits. The access address for all advertising channel data packets is predetermined by the BLE protocol. The access address in data channel packets is generated by the device and is different for any two devices using the same data channel. The PDU contains a 16 bit header and a variable size payload. Optionally, the PDU for data channel data packets may contain a 32 bit Message Integrity Check field for use in encrypting data packets.

Each device using the BLE protocol is designated either as a master or a slave device. The BLE protocol does not limit the number of slave devices controlled or communicating with the master device. Once communication is established, the master and the slave alternate sending and receiving data packets during a connection event. The connection event may last between 7.5 ms to 4.0 s and beginning at an anchor point. The anchor point is derived on when the master device transmits a data channel PDU to the slave device. Either the master or slave device may close or terminate the connection event.

A technical effect of various embodiments described herein extend the communication range and signal quality of the IMD in relation to the patient. A technical effect of various embodiments described herein provide a wireless bridge device implemented on a single SoC reducing cost and complexity in firmware design.

FIG. 1 illustrates a simplified block diagram of a system 100 for bridging a bi-directional communication link between an external device 201 and an implantable medical device (IMD) 101. The system 100 includes the implantable medical device (IMD) 101 having a bi-directional communication link 104 with a wireless bridge device 102, and the external device 201 (e.g., table computer, smart phone, laptop, or the like) having a bi-directional communication link 105 with the wireless bridge device 102.

The bi-directional communication links 104 and 105 may use any standard wireless protocol such as Bluetooth Low Energy, Bluetooth, Wireless USB, Medical Implant Communication Service, ZigBee, and/or the like that define a means for transmitting and receiving information (e.g., data, commands, instructions) between devices. For example, the wireless bridge device 102 may receive and/or transmit information to the external device 201 via the bi-directional communication link 105. In another example, the wireless bridge device 102 may receive and/or transmit information to the IMD 101 via the bi-directional communication link 104.

The external device 201 may program the IMD 101 and/or receive data from the IMD 101 via the wireless bridge device 102, which provides a communication bridge between the IMD 101 and the external device 201. For example, the external device 201 may transmit a request for data measurements over the bi-directional communication link 105. The request is received by the wireless bridge device 102, which relays (e.g., transmits) the request for data measurements to the IMD 101 over the bi-directional communication link 104. In response to the request, the IMD 101 transmits the measurements to the wireless bridge device 102 over the bi-directional communication link 104. The wireless bridge device 102 relays (e.g., transmits) the measurements to the external device 201 over the bi-directional communication link 105.

In various embodiments, the wireless bridge device 102 may be portable and/or handheld device allowing the user to position and/or reposition the wireless bridge device 102 within a room and/or in varying proximities to the patient. For example, the wireless bridge device 102 may be placed against an exterior surface of the patient 106, such as the skin of a patient 106. Additionally or alternatively, the wireless bridge device 102 may be mounted and/or integrated to a device proximate to the patient 106. For example, the wireless bridge device 102 may be mounted to a bed of the patient 106, a patient monitoring system, and/or the like.

The IMD 101 may be implanted within the patient 106 (e.g., proximate to a heart 103, proximate to the spinal cord). Additionally or alternatively, the IMD 101 may have components that are external to the patient 106, for example, the IMD 101 may include a neuro external pulse generator (EPG). The IMD 101 may be one of various types of implantable devices, such as, for example, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like.

Figure 2:
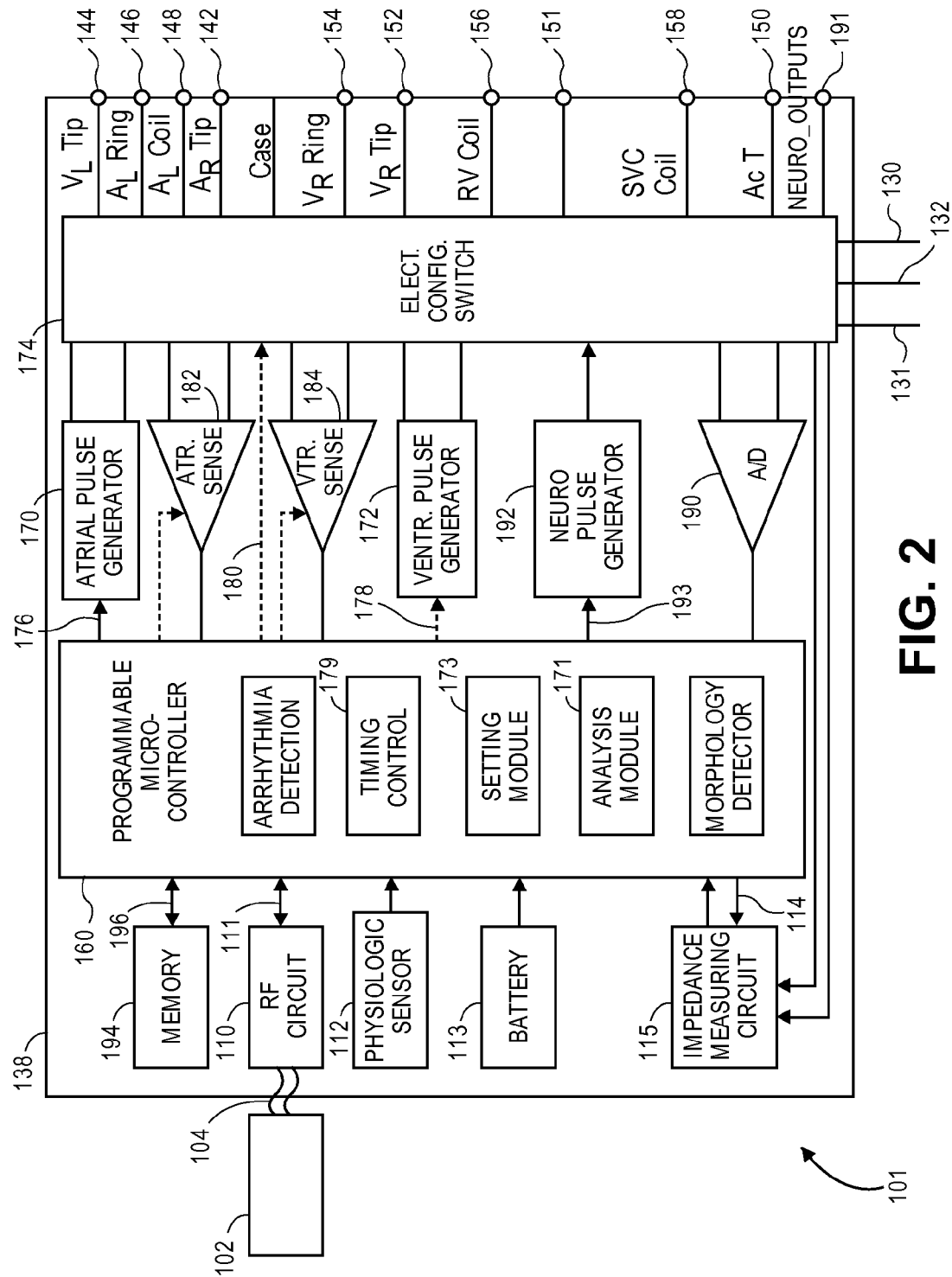
FIG. 2 illustrates a block diagram of exemplary internal components of an implantable medical device, according to an embodiment of the present disclosure.

FIG. 2 illustrates a block diagram of exemplary internal components of the IMD 101. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 101 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. Additionally or alternatively, the IMD 101 may be used to generate electrical stimulation for application to a desired area of a body, such as a spinal cord stimulation, as described later herein corresponding to FIG. 9.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals, 142, 152, 154, 156 and 158 (shown schematically and, for convenience, the names of the electrodes to which they are connected are shown next to the terminals. A right atrial tip terminal ($A_R$ TIP) 142 is adapted for connection to the atrial tip electrode and a right atrial ring terminal may be adapted for connection to right atrial ring electrode. A left ventricular tip terminal ($V_L$ TIP) 144, a left atrial ring terminal ($A_L$ RING) 146, and a left atrial shocking terminal ($A_L$ COIL) 148 are adapted for connection to the left ventricular ring electrode, and a left atrial tip electrode and a left atrial coil electrode respectively. A right ventricular tip terminal ($V_R$ TIP) 152, a right ventricular ring terminal ($V_R$ RING) 154, a right ventricular shocking terminal ($R_V$ COIL) 156, and an SVC shocking terminal (SVC COIL) 158 are adapted for connection to the right ventricular tip electrode, right ventricular ring electrode, an RV coil electrode, and an SVC coil electrode, respectively.

An acoustic terminal (ACT) 150 is adapted to be connected to an external acoustic sensor or an internal acoustic sensor, depending upon which (if any) acoustic sensors are used. Terminal 151 is adapted to be connected to a blood sensor to collect measurements associated with glucose levels, natriuretic peptide levels, or catecholamine levels.

The IMD 101 includes a programmable microcontroller 160 which controls operation. The microcontroller 160 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 160 includes the ability to process or monitor input signals (data) as controlled by program code stored in memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes. For example, the cardiac data sets may include IEGM data, pressure data, heart sound data, and the like.

The IMD 101 includes an atrial pulse generator 170 and a ventricular/impedance pulse generator 172 to generate pacing stimulation pulses for delivery by the right atrial lead 130, the right ventricular lead 131, and/or the coronary sinus lead 132 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the microcontroller 160 via appropriate control signals, 176 and 178, respectively, to trigger or inhibit the stimulation pulses.

The IMD 101 includes a neuro stimulation pulse generator circuit 192 to generate stimulation pulses for a brain or spinal cord nervous system. The stimulation pulses are delivered by a plurality of electrodes through the neuro output lead 191. The neuro stimulation pulse generator circuit 192 is controlled by the microcontroller 160 via appropriate control signals 193 to trigger or generate the stimulation pulses.

The microcontroller 160 further includes timing control circuitry 179 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the microcontroller 160, determines the polarity of the stimulation pulses (e.g., unipolar, bipolar, etc.) by selectively closing the appropriate combination of switches (not shown) as is known in the art.

Atrial sensing circuit 182 and ventricular sensing circuit 184 may also be selectively coupled to the right atrial lead 130, coronary sinus lead 132, and the right ventricular lead 131, through the switch 174 for detecting the presence of cardiac activity in each of the four chambers of the heart. Accordingly, the atrial (ATR SENSE) and ventricular (VTR SENSE) sensing circuits, 182 and 184, may include dedicated sense amplifiers, multiplexed amplifiers or shared amplifiers. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are also applied to the inputs of an analog-to-digital (A/D) data acquisition system 190. The data acquisition system 190 is configured to acquire IEGM signals, convert the raw analog data into a digital IEGM signal, and store the digital IEGM signals in memory 194 for later processing and/or RF transmission along the bi-directional communication link 104. The data acquisition system 190 is coupled to the right atrial lead 130, the coronary sinus lead 132, and the right ventricular lead 131 through the switch 174 to sample cardiac signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The controller 160 controls the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The S1 segment is associated with initial systole activity. The S2 segment is associated with initial diastole activity. The linking segment is associated with at least a portion of heart activity occurring between the S1 and S2 segments during a systolic interval between the initial systole and diastole activity. The controller 160 changes a value for at least one of the pacing parameters between the cardiac cycles. The controller 160 implements one or more processes described herein to determine values for one or more pacing parameters that yield a desired level of hemodynamic performance.

The controller 160 includes an analysis module 171 and a setting module 173 that function in accordance with embodiments described herein. The analysis module 171 analyzes a characteristic of interest from the heart sounds within at least a portion of the linking segment. The characteristic of interest is indicative of an "amount" of the heart sounds over at least a portion of the systolic interval between the initial systole and diastole activity. The amount of the heart sounds may be derived in different manners, such as determining the energy content, intensity and the like, as well as relations there between. The level of the characteristic changes as the pacing parameter is changed. The setting module 173 sets a desired value for the pacing parameter based on the characteristic of interest from the heart sounds for at least the portion of the linking segment. The pacing parameter may represent at least one of an AV delay, a VV delay, a VA delay, intra-ventricular delays, electrode configurations and the like. The controller 160 changes at least one of the AV delay, the VV delay, the VA delay, the intra-ventricular delays, electrode configurations and like in order to reduce systolic turbulence and regurgitation.

The RF circuit 110 may be configured to handle and/or manage the bi-directional communication link between the IMD 101 and the wireless bridge device 102. The RF circuit 110 is controlled by the microcontroller 160 and may support a particular wireless communication protocol while communicating with the wireless bridge device 102, such as Bluetooth low energy, Bluetooth, ZigBee, Medical Implant Communication Service (MICS), or the like. Protocol firmware may be stored in memory 194, which is accessed by the microcontroller 160. The protocol firmware provides the wireless protocol syntax for the controller 160 to assemble data packets, establish communication links 104, and/or partition data received from the wireless bridge device 102.

The microcontroller 160 is coupled to memory 194 by a suitable data/address bus 196, wherein the programmable operating parameters used by the microcontroller 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, SvO2 data and the like for a desired period of time (e.g., 1 hour, 24 hours, 1 month). The memory 194 may store instructions to direct the microcontroller 160 to analyze the cardiac signals and heart sounds identify characteristics of interest and derive values for predetermined statistical parameters. The IEGM, pressure, and heart sound data stored in memory 194 may be selectively stored at certain time intervals, such as 5 minutes to 1 hour periodically or surrounding a particular type of arrhythmia of other irregularity in the heart cycle. For example, the memory 194 may store data for multiple non-consecutive 10 minute intervals.

The memory 194 may also contain a pre-defined algorithm that generates a passkey. The passkey may be used during a pairing and/or bonding procedure between the IMD 101 and the wireless bridge device 102 to establish the bi-directional communication link 104. The passkey may be generated based on connection identification information. The connection identification information may include a dynamic seed and/or a static identification or encrypted static identification transmitted by the RF circuit 110 through the bi-directional communication link 104 from the wireless bridge device 102 and inputted into the pre-defined algorithm. Optionally, the dynamic seed may be a random number generated by the microcontroller 160, based on the local system clock of the IMD 101, or the like that is transmitted by the RF circuit 110 to the wireless bridge device 102. Additionally or alternatively, the static identification may be stored on the memory 194 representing a product serial identification number of the IMD 101, which is a unique number assigned to the IMD 101 by a manufacturer of the IMD 101. Optionally, the static identification may be a pre-determined number stored on the memory 194 set by a user.

The pacing and other operating parameters of the IMD 101 may be non-invasively programmed into the memory 194 through the RF circuit 110 via the bi-directional communication link 104. The RF circuit 110 is controlled by the microcontroller 160 and receives data for transmission by a control signal 111. The RF circuit 110 allows intra-cardiac electrograms, pressure data, acoustic data, SvO2 data, and status information relating to the operation of IMD 101 (as contained in the microcontroller 160 or memory 194) to be sent to the wireless bridge device 102 through the established bi-directional communication link 104. The RF circuit 110 also allows new pacing parameters for the setting module 173 used by the IMD 101 to be programmed through the bi-directional communication link 104.

To establish the bi-directional communication link 104 between the wireless bridge device 102 and the IMD 101, the microcontroller 160 may enter an advertisement mode by instructing the RF circuit 110 to transmit or broadcast one or more advertisement notices along a dedicated advertisement channel defined by the wireless protocol. The advertisement channel is a point to multipoint, unidirectional, channel to carry a repeating pattern of system information messages such as network identification, allowable RF channels to establish the bi-directional communication link 104, and/or the like that is included within the advertisement notice. The advertisement notice may be repeatedly transmitted after a set duration or an advertisement period until the bi-directional communication link 104 is established with the wireless bridge device 102.

Optionally, the length of the advertisement period may be adjusted by the microcontroller 160 during a select advertisement mode. For example, during the select advertisement mode the microcontroller 160 may reduce the length of the advertisement period relative to not being in the select advertisement mode. The reduced length of the advertisement period results in the RF circuit 110 transmitting more or an increased number of advertisement notices relative to not being in the select advertisement mode.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

The physiologic sensor 112 may be used as the acoustic sensor that is configured to detect the heart sounds. For example, the physiologic sensor 112 may be an accelerometer that is operated to detect acoustic waves produced by blood turbulence and vibration of the cardiac structures within the heart (e.g., valve movement, contraction and relaxation of chamber walls and the like). When the physiologic sensor 112 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. The IMD 101 is shown as having impedance measuring circuit 115 which is enabled by the microcontroller 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
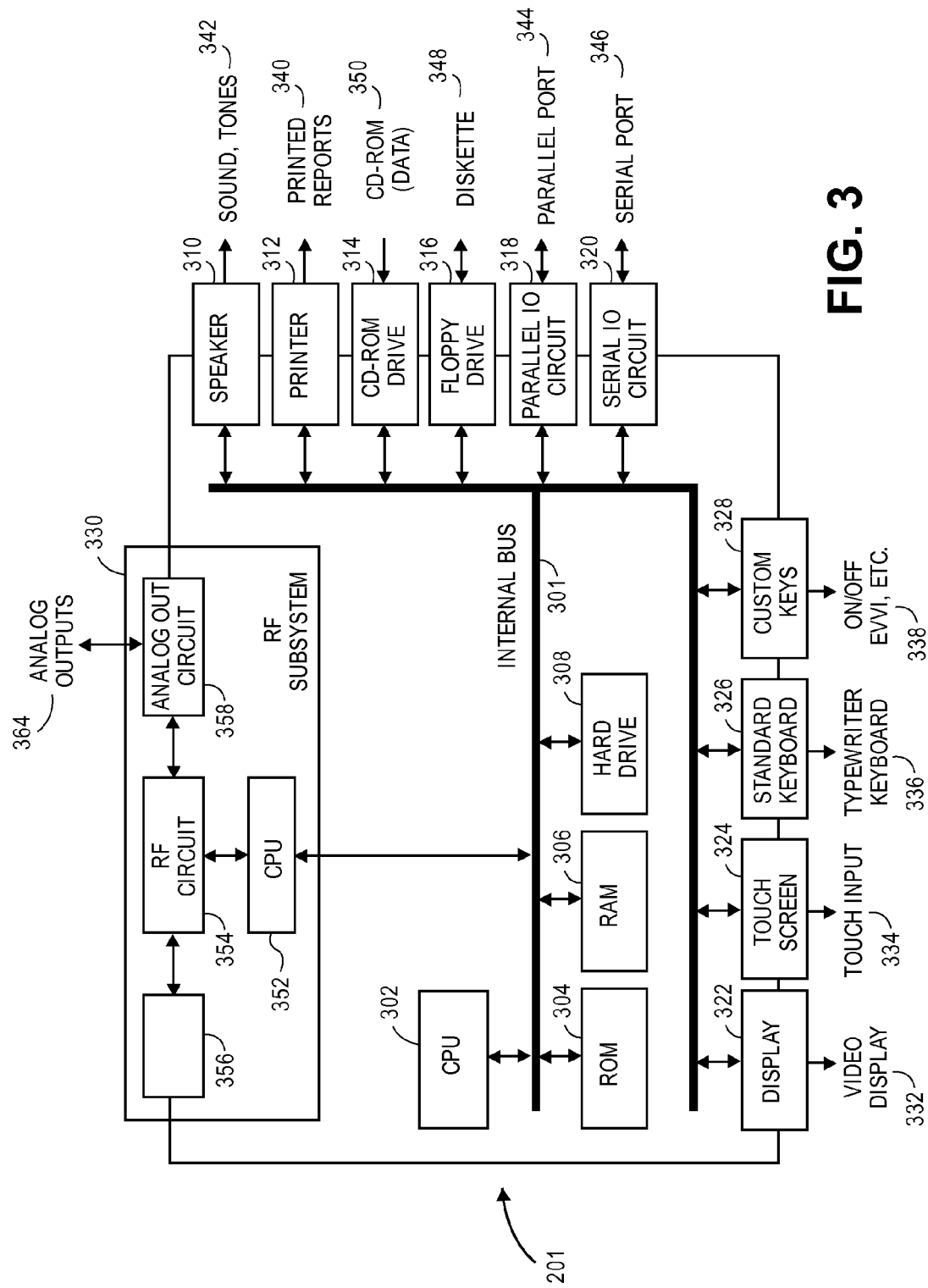
FIG. 3 illustrates a block diagram of exemplary internal components of an external device, according to an embodiment of the present disclosure.

FIG. 3 illustrates a functional block diagram of the external device 201 that is operated in accordance with the processes described herein and to interface with the wireless bridge device 102 and/or the IMD 101 as described herein. The external device 201 may be a workstation, a portable computer, a tablet computer, an IMD programmer, a PDA, a cell phone and/or the like located within a home of the patient 106, a hospital or clinic, an automobile, at an office of the patient, or the like.

The external device 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a microcontroller, or equivalent control circuitry, designed specifically to control interfacing with the external device 201 and with the wireless bridge device 102 and/or the IMD 101. The CPU 302 may include RAM or ROM memory, logic and timing circuitry, state machine circuitry, and I/O circuitry to interface with the wireless bridge device 102 and/or the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external device 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the external device 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The external device 201 may wirelessly communicate with the wireless bridge device 102 and utilize protocols, such as Bluetooth, Bluetooth low energy, ZigBee, MICS, and the like.

Figure 4A:
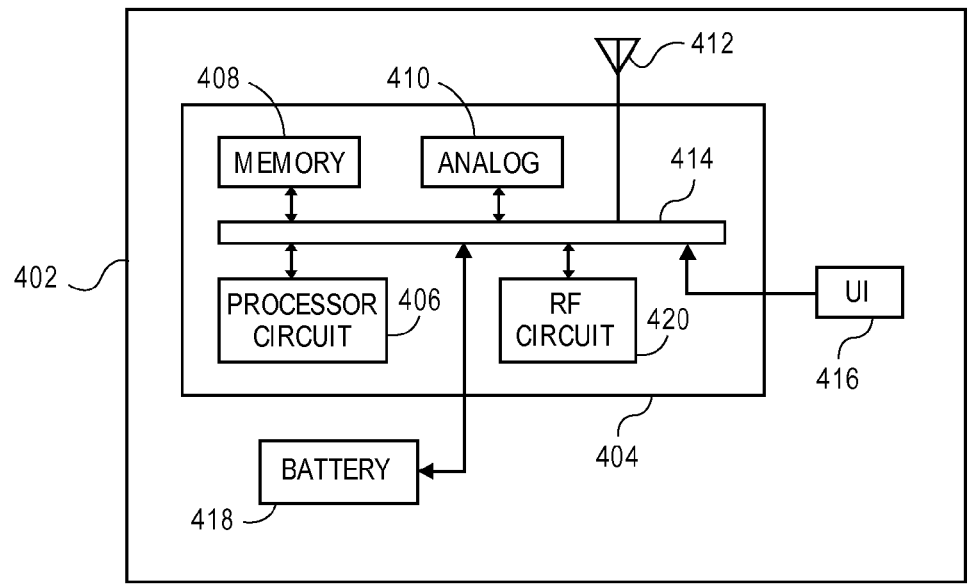
FIG. 4A illustrates a block diagram of exemplary internal components of a wireless bridge device, according to an embodiment of the present disclosure.
Figure 4B:
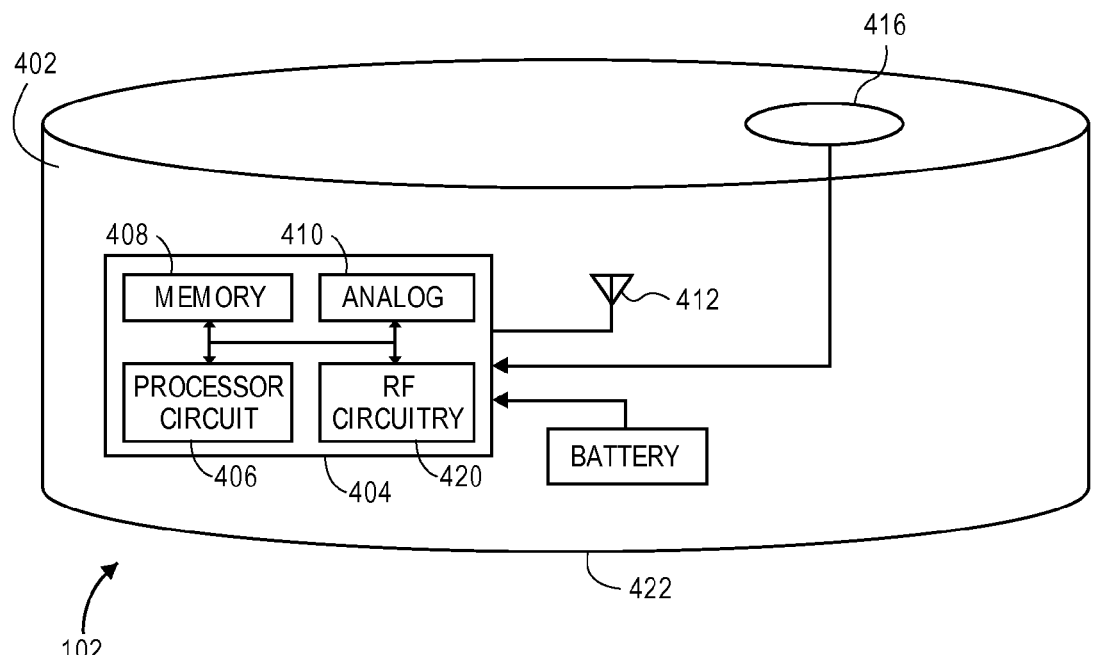
FIG. 4B illustrates a block diagram of exemplary internal components of a wireless bridge device, according to an embodiment of the present disclosure.

FIGS. 4A-B illustrates a functional block diagram of the wireless bridge device 102. It should be noted that the wireless bridge device 102 is for illustration purposes only, and it is understood that the circuitry and/or components may be duplicated, eliminated or disabled in any desired combination thereof.

In the illustrated embodiment shown in FIGS. 4A-B, the wireless bridge device 102 may include a housing 402 that encloses an antenna 412, a battery 418 or power source, and a system on chip (SoC) 404. The housing 402 may be comprised of a plastic and/or other non-conductive material. The housing 402 may be configured to be handheld by the user and/or configured to be placed against an exterior surface of the patient 106 (e.g., the skin of the patient). The battery 418 provides operating power to the SoC 404. Optionally, the antenna 412 may be positioned on the exterior surface of the housing 402.

The SoC 404 may include a memory module 408, an input/output (I/O) interface 414, a processor circuit 406, analog circuitry 410, and an RF circuit 420. Optionally, the SoC 404 may be a Bluetooth Low Energy System on Chip. For example, the RF circuit 420, the memory module 408, and the processor circuit 406 may be designed for operating under the BLE wireless protocol.

The SoC 404 may be an integrated circuit (IC) such that all components of the SoC 404 are on a single chip substrate (e.g., a single silicon die, a chip). For example, the SoC 404 may have the memory module 408, the I/O interface 414, the processor circuit 406, and the analog circuitry 410 embedded on a single die contained within a single chip package (e.g., QFN, TQFP, SOIC, BGA, and/or the like).

Additionally or alternatively, the SoC 404 may comprise a plurality of chips (e.g., silicon dies, ICs) stacked within a single chip package. For example, the analog circuitry 410 and the processor circuit 406 are two different ICs. The ICs are stacked vertically on a substrate within a single chip package. Each IC is internally connected to each other and/or bonded by wire to the single chip package.

Additionally or alternatively, the SoC 404 may represent a plurality of discrete integrated circuit packages (e.g., the memory module 408, the I/O interface for 414, the analog circuitry 410, the RF circuit 420) stacked vertically to reduce PCB area. For example, the analog circuitry 410 and the processor circuit 406 may each be in a ball grid array (BGA) package, respectively, which has interconnection pins along the bottom surface of each BGA package. The BGA package of the analog circuitry 410 is coupled to a printed circuit board (PCB) of the wireless bridge device 102, and has an extended substrate around the BGA package. The BGA package of the processors circuit 406 is vertically stacked atop of the BGA package of the analog circuitry 410 having the interconnection pins of the processors circuit 406 coupled to the extended substrate. Thereby, the only PCB footprint is the BGA package of the analog circuitry 410.

The analog circuitry 410 may include amplifiers, filters, analog to digital converters, memory storage devices, digital signal processors and/or the like. Optionally, the analog circuitry 410 may be integrated with the RF circuit 420.

The memory module 408 may include EEPROM, RAM, ROM, flash, and/or a hard drive. The memory module 408 may include protocol firmware that may be accessed by the processor circuit 406. The protocol firmware may provide the wireless protocol syntax for the processor circuit 406 to assembler data packets, establish the bi-directional communication links 104 and 105 based on the wireless protocol, partition data from the data packets, and/or the like. The protocol syntax may include specifications on the structure of packets (e.g., frame size, packet specifications, appropriate number of bits, frequency, and/or the like) such as advertisement notices or data packets that are received and/or transmitted by the wireless bridge device 102.

The protocol syntax may further include a time slice algorithm. The time slice algorithm may subdivide a communication interval (e.g., similar to the connection event, the communication interval 732 of FIG. 7) into one or more time slices when the wireless bridge device 102 has concurrent and/or simultaneous bi-directional communication links 104 and 105. During the communication interval the external device 201 and the wireless bridge device 102 exchange data packets along the bi-directional communication link 105. A length of the communication interval may be defined by the wireless protocol and/or the external device 102 corresponding to a length of time for the wireless bridge device 102 to respond to a data packet transmitted from the external device 201. Additionally or alternatively, if the external device 201 does not receive a data packet from the wireless bridge device 102 during the communication interval, the external device 201 may terminate and/or close down the bi-directional communication link 105.

During the communication interval, while the wireless bridge device 102 has concurrent and/or simultaneous bi-directional communication links 104 and 105, the wireless bridge device 102 and the IMD 101 may exchange data packets along the bi-directional communication link 104. The exchange of data packets between the wireless bridge device 102 and the IMD 101 occurs prior to the wireless bridge device 102 transmits a data packet (e.g., completing the exchange) to the external device 201. For example, the external device 201 transmits a first data packet to the wireless bridge device 102. The wireless bridge device 102 relays (e.g., transmits) the first data packet to the IMD 101. The IMD 101 receives the first data packet and transmits a response data packet to the wireless bridge device 102. The wireless bridge device 102 receives the response data packet and relays (e.g., transmits) the response data to the external device 201, within the communication interval.

The time slices correspond to when transmission data packets from the wireless bridge device 102 may be transmitted over the bi-directional communication links 104 and/or 105, received by the wireless bridge device 102, and/or the like. The time slices enable the exchanges of data packets between the wireless bridge device 102, the IMD 101, and the external device 201 to be within the communication interval maintaining the bi-directional communication links 104 and 105 concurrently and/or simultaneously. For example, a first time slice may correspond to when the wireless bridge device 102 can relay (e.g., transmit) a data pack received by the external device 201 to the IMD 101, a second time slice may correspond to when the wireless bridge device 102 may receive a response data packet from the IMD 101, and a third time slice may correspond to when the wireless bridge device may relay (e.g., transmit) the response data packet to the external device 201. It should be noted that in various embodiments the communication interval may be subdivided equally such that the time slices have approximately the same or equal lengths.

Additionally or alternatively, at least two of the time slices may have different lengths. For example, a time slice corresponding to the transmission of a data packet from the wireless bridge device 102 to the IMD 101 may be larger relative to the time slices corresponding transmissions of data packets from the IMD 101 to the wireless bridge device 102 and from the wireless bridge device 102 to the external device 201. In another example, a time slices corresponding to the transmission of data packets from the IMD 101 to the wireless bridge device 102 and from the wireless bridge device 102 to the external device 201 may be larger relative to the time slice corresponding to the transmission of a data packet from the wireless bridge device 102 to the IMD 101.

A length of the time slices may be based on the length of the communication interval, a size of the data packet received by the wireless bridge device 102 from the external device, and/or the like. For example, time slices may be longer when subdivided from communication intervals having a longer length relative to a shorter communication interval.

Figure 7:
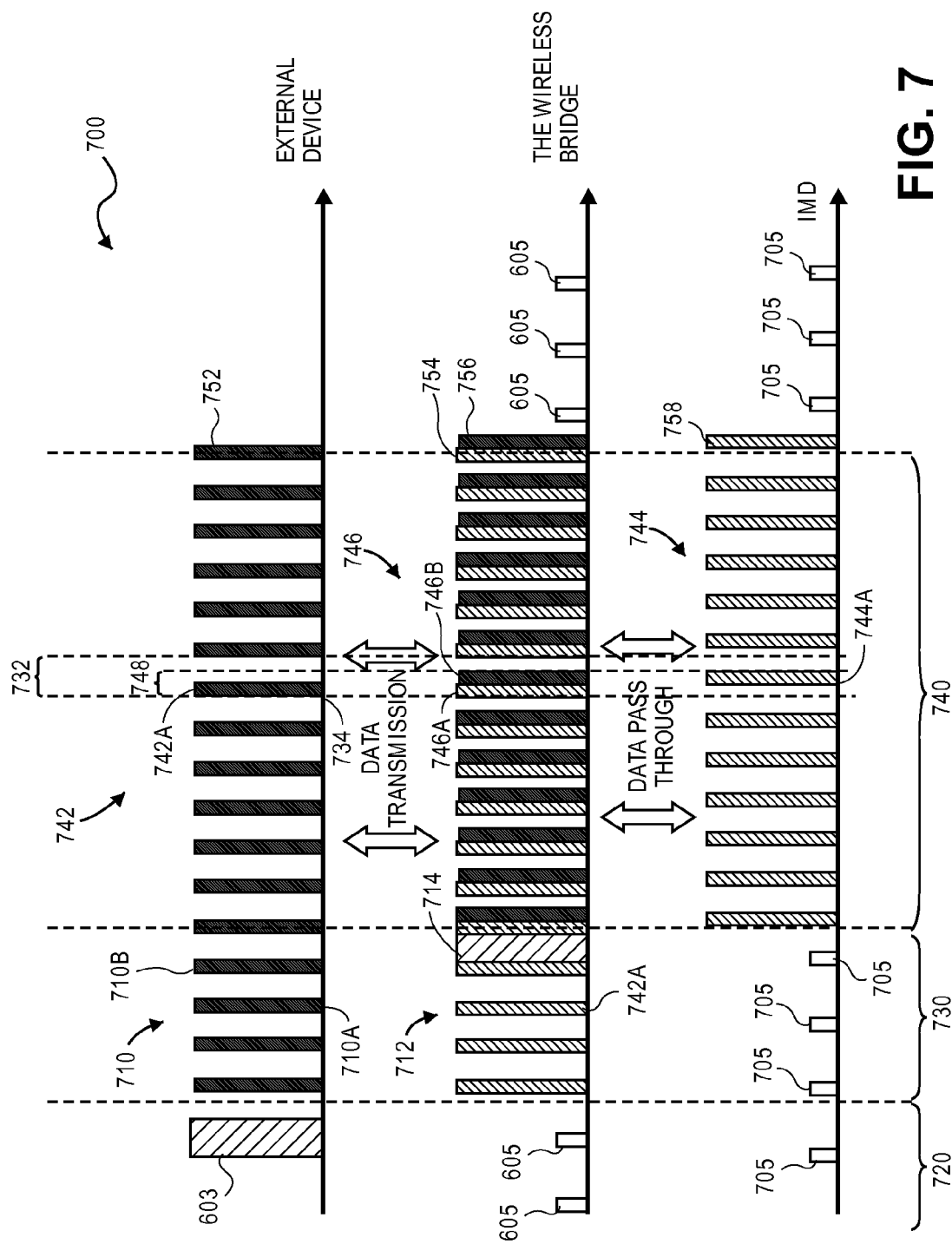
FIG. 7 illustrates a timing diagram between an external device, a wireless bridge device, and an implantable medical device, according to an embodiment of the present disclosure.

Optionally, one of the time slices may correspond to a second communication interval (e.g., 748 of FIG. 7). For example, the second communication interval may be defined by the wireless bridge device 102 corresponding to a length of time for the IMD 101 to respond to a data packet transmitted from the wireless bridge device 102. The second communication interval may be within the communication interval between the wireless bridge device 102 and the external device 201.

Returning to FIGS. 4A and 4B, the RF circuit 420 of the wireless bridge device 102 may include a transceiver or transmitter-receiver that includes an oscillator, a modulator, a demodulator, one or more amplifiers, an impedance circuit, and/or the like. The RF circuit 420 allows the wireless bridge device 102 to facilitate telemetry to establish one or more bi-directional communication links 104, 105 using the wireless communication protocol such as BLE, Bluetooth, ZigBee, or the like via the antenna 412.

The antenna 412 may be an omnidirectional antenna such that the antenna 412 radiates and/or receives RF electromagnetic fields uniformly or equally in all directions. Thereby, the antenna 412 may transmit and/or receive wireless communications equally without limiting a position of the wireless bridge device 102 with respect to the external device 201 and/or the IMD 101. The antenna 412 may be tuned to a predetermined resonant frequency such that the antenna 412 has a signal performance exhibiting a lower return loss at a predetermined resonant frequency relative to alternative frequencies, such as a resonant frequency of the wireless protocol. For example, the wireless protocol may correspond to the BLE protocol that operates in a 2.4 GHz band. The antenna 412 may be configured from a shape of the antenna 412 (e.g., length, cross-sectional thickness, area) and/or by coupling components to the antenna 412 (e.g., capacitor, inductor) to achieve the resonant frequency of 2.4 GHz.

Optionally, the wireless bridge device 102 may include additional antennas. For example, the wireless bridge device 102 may include a directional antenna (not shown) configured for the bi-directional communication link 104 with the IMD 101 while the antenna 412 may be for the bi-directional communication link 105 with the external device 201. The directional antenna may be configured to radiate and/or receive more RF electromagnetic fields in one or more directions relative to other directions.

For example, the IMD 101 may be embedded within the chest of the patient 106. As shown in FIG. 4B, the housing 402 of the wireless bridge device 102 may include a flat surface 422 area along a horizontal plane. The flat surface 422 may allow the wireless bridge device 102 to be positioned on a chest of the patient 106 such that the flat surface 422 and the chest of the patient 106 are in contact. The position of the wireless bridge device 102 on the chest of the patient 106 allows the wireless bridge device 102 to be positioned proximate to the IMD 101. The directional antenna may be configured to direct and/or receive RF electromagnetic fields along a directional vector that extends perpendicular from the surface area of the flat surface 422 towards the chest of the patient 106. Thereby, the directional antenna may radiate and receive more RF electromagnetic fields towards/from the chest, including the direction of the IMD 101, relative to other directions along the surface area of the housing 402.

As depicted in FIG. 4A, the I/O interface 414 may be an interconnect or bus that electrically couples the memory module 408, the analog circuitry 410, and the processor circuit 406 with each other. The I/O interface 414 enables data and/or instructions to be delivered and/or received between the processor circuit 406, the memory module 408, and the analog circuitry 410. Additionally or alternatively, the I/O interface 414 may electrically couple the SoC 404 with peripheral components of the SoC 404 such as the antenna 412, the battery 418, and a user interface component 416.

The processor circuit 406 may include one or more processors or microprocessors, or equivalent control circuitry, designed for controlling the components of the wireless bridge device 102. Optionally the processor circuit 406 may include EEPROM, RAM or ROM memory, logic and timing circuitry, state machine circuitry, and I/O circuitry. The processor circuit 406 may process and/or monitor input signals (data) received via the I/O interface 414 as controlled by executing program code stored on the memory included within the processor circuit 406 and/or the memory module 408.

Additionally or alternatively, the housing 402 may include a user interface component 416, such as a button, a tactile switch, or the like on the housing 402, such as shown in FIG. 4B. The user interface component 416 may be configured to activate and/or de-activate the wireless bridge device 102. For example, when the wireless bridge device 102 is positioned proximately to the IMD 101, such as on the chest of the patient 106, a user may turn on the wireless bridge device 102 using the user interface component 416.

Figure 5:
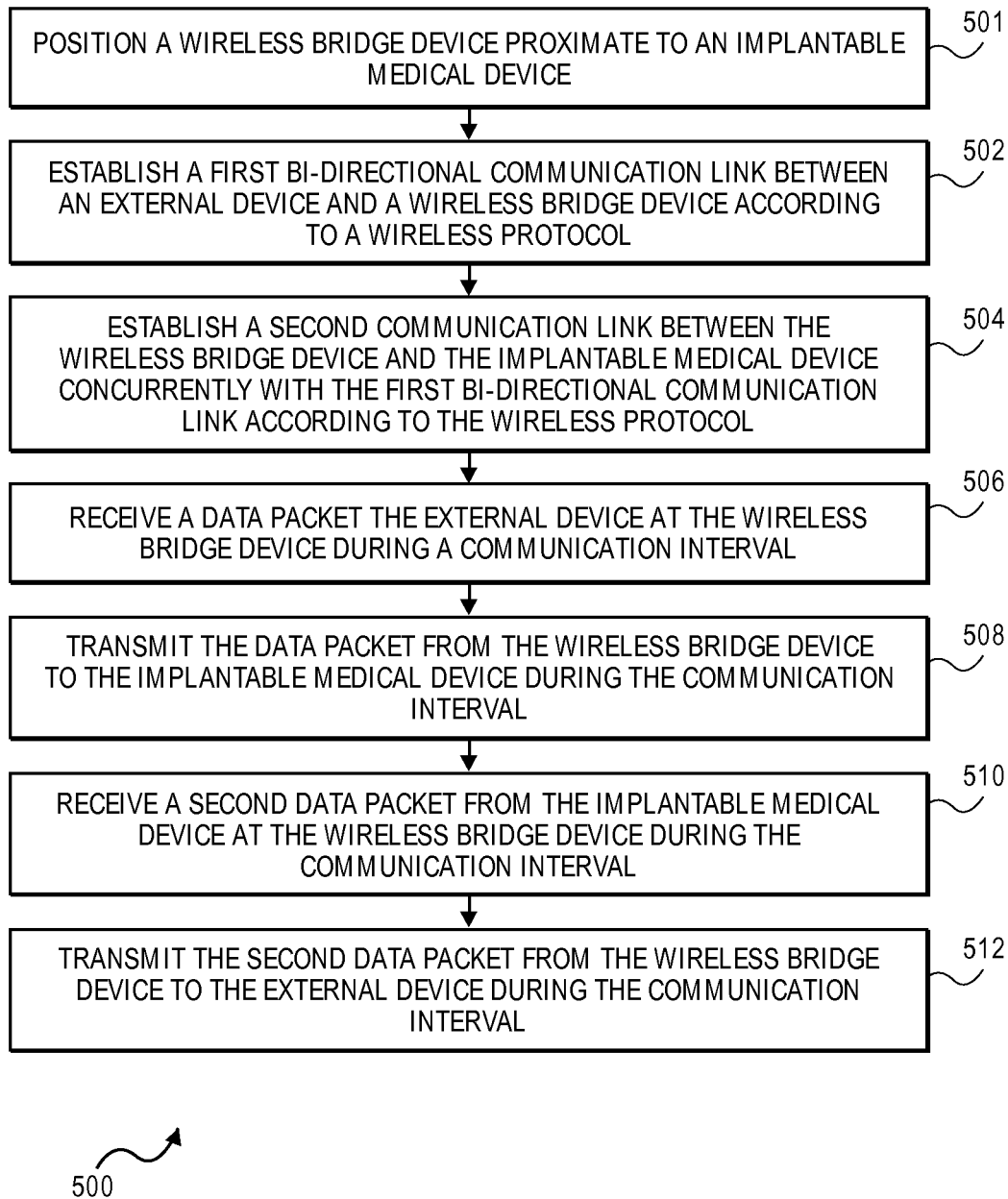
FIG. 5 illustrates a flowchart of a method for bridging a bi-directional communication link between an external device and an implantable medical device.
Figure 8:
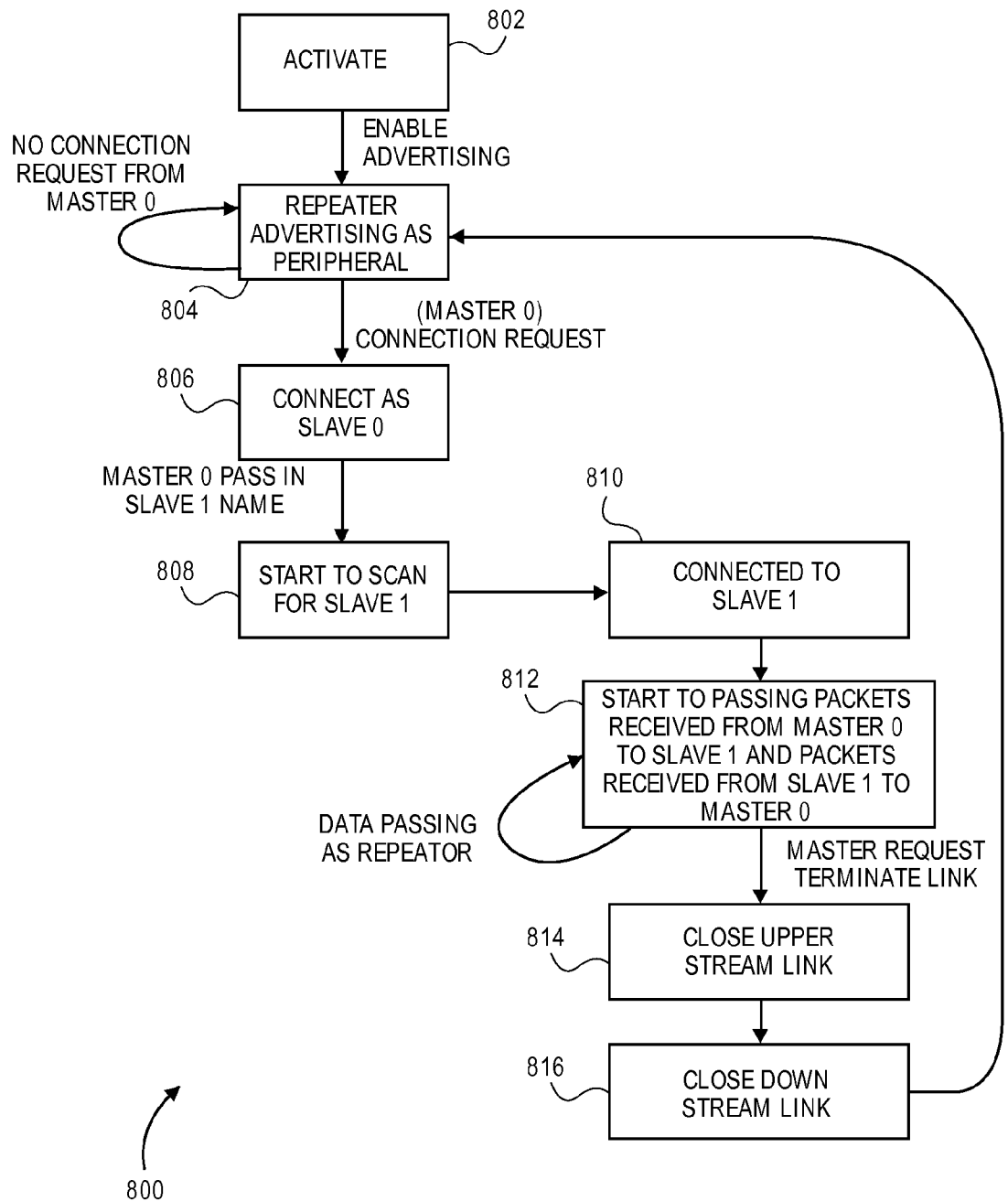
FIG. 8 illustrates a flowchart of a method for bridging a bi-directional communication link between an external device and an implantable medical device.

FIGS. 5 and 8 illustrate flowcharts of methods 500 and 800 for bridging a bi-directional communication link between an external device (e.g., 201) and an implantable medical device (IMD) (e.g., 101). The methods 500 and 800 may be implemented as a software algorithm, package, or system that directs one or more hardware circuits or circuitry to perform the actions described herein. For example, the operations of the methods 500 and 800 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes i) establishing a first bi-directional communication link between an external device and a wireless bridge device according to a wireless protocol, ii) establishing a second bi-directional communication link between the wireless bridge device and an IMD concurrently with the first bi-directional communication link according to the wireless protocol, iii) receiving a data packet from the external device at the wireless bridge device, and/or iv) transmitting the data packet from the wireless bridge device to the IMD during a communication interval.

Beginning at 501, the wireless bridge device 102 is positioned proximate to the IMD 101. For example the wireless bridge device 102 may be positioned against an exterior surface of the patient 106, such as the skin of the patient 106, approximate to a position of the IMD 101 with respect to the patient. Additionally or alternatively, the patient 106 may be moved such that a positioned of the wireless bridge device 102 is proximate to the IMD 101. For example, the wireless bridge device 102 may be mounted and/or stationary, such as mounted to a bed of the patient 106, within a patient monitoring system, and/or the like. The patient 106 may be moved to a location proximate to the wireless bridge device 102 (e.g., seated and/or lying on the bed) to position the wireless bridge device 102 proximate to the IMD 101.

At 502, a first bi-directional communication link (e.g., the bi-directional communication link 105) is established between the external device 201 and the wireless bridge device 102 according to the wireless protocol.

For example, a user and/or patient may activate the wireless bridge device 201 using the user interface component 416. When activated, the SoC 404 may enter a powered state. During the powered state, the battery 418 may provide electric current and/or voltage potential to the SoC 404 enabling the wireless bridge device 201 to establish one or more bi-directional communication links by entering an advertisement mode. During the advertisement mode the wireless bridge device 201 broadcasts one or more advertisement notices 605 along a dedicated advertisement channel defined by the wireless protocol.

Figure 6:
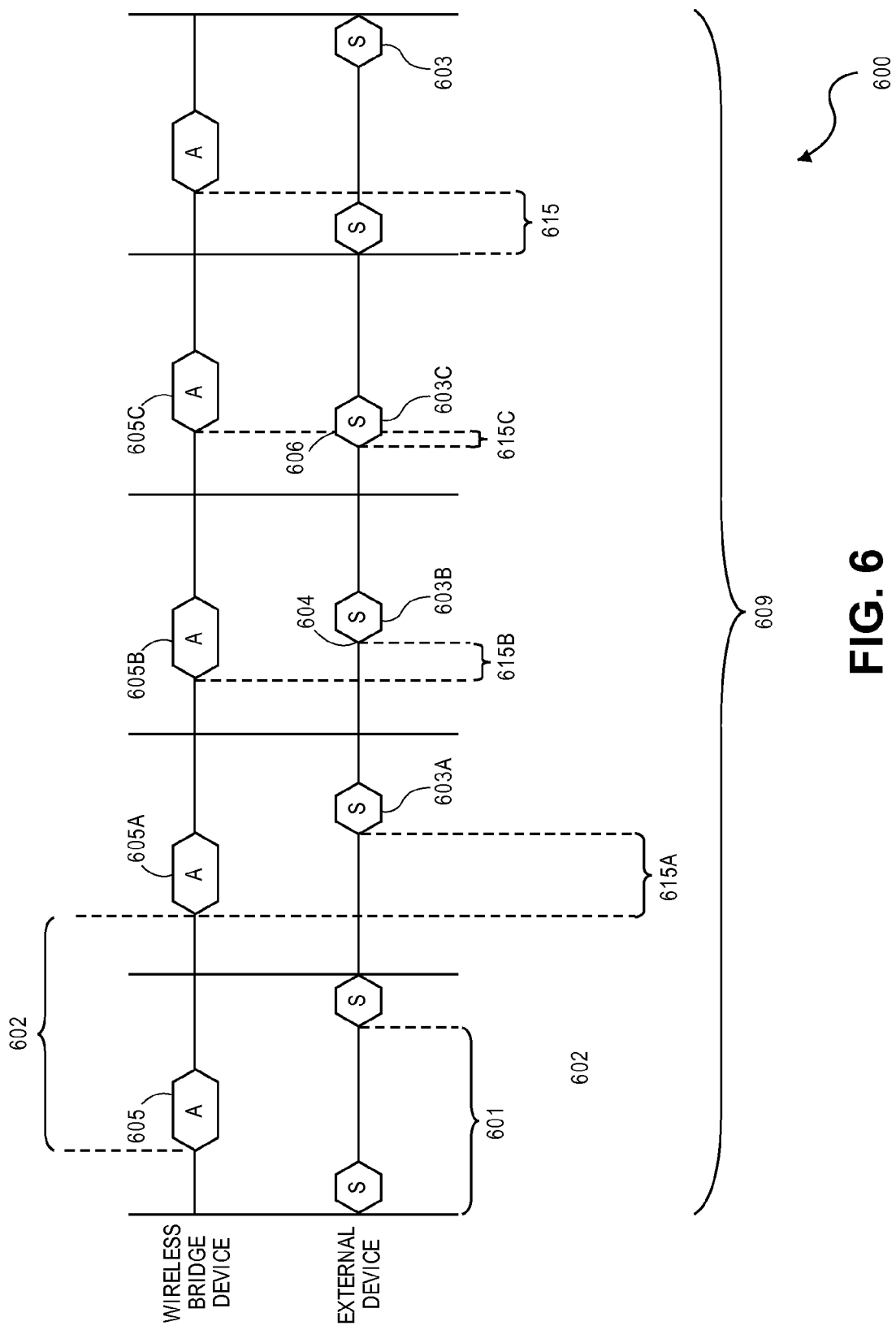
FIG. 6 illustrates a timing diagram to establish a communication link, according to an embodiment of the present disclosure.

FIG. 6 illustrates a timing diagram 600 to establish the bi-directional communication link 105 between the wireless bridge device 102 and the external device 201, according to an embodiment of the present disclosure. The wireless bridge device 102 and the external device 201 use a wireless protocol (e.g., BLE) that utilizes a dedicated frequency and/or frequency channels for one or more advertisement channels. The wireless bridge device 102 transmits an advertisement notice 605 along one or more of the advertisement channels using the RF circuit 420.

The advertisement notice 605 represents a data packet that may contain frequency synchronization information utilized to form the bi-directional communication link 105, address information of the wireless bridge device 102, address information of the external device 201, and/or the like as defined by the wireless protocol. Additionally or alternatively, the advertisement notice 605 may include pairing and/or bondable information (e.g., passkey seed information). The advertisement notice 605 may be repeated, at a set or variable interval or an advertisement period 602, until the bi-directional communication link 105 is established. The advertisement period 602 represents a length of time between advertisement notices 605 transmitted by the wireless bridge device 102.

For example, the advertisement period 602 may be 5 seconds such that the advertisement notice 605 may be repeated every 5 seconds. Optionally, the advertisement period 602 may be longer or shorter than the above example. The advertisement period may be predetermined and stored in the memory module 408. Optionally, the advertisement period 602 may be input by a user (e.g., physician or clinician using the user interface component 416).

The external device 201 monitors the one or more advertisement channels during a scanning interval 603 to detect one or more of the advertisement notices 605. The scanning interval 603 may be initiated by the user. For example, the user, using the touchscreen 324 or standard keyboard 336, may instruct the external device 201 to establish the bi-directional communication link 105. The CPU 302 (FIG. 3) of the external device 201 instructs the RF subsystem 330 to monitor one or more advertisement channels, for example, every 1 s corresponding to the scanning interval 603. The RF subsystem repeats the scanning interval 603 every scan period 601 such that the scanning interval 603 may be repeated, for example, every 4 s. For example, the scan period 601 represents a length of time between scan intervals. The scanning interval 603 and/or scan period 601 may be longer or shorter than the above example. Additionally or alternatively, the scanning interval 603 and/or scan period 601 may be a predetermined length stored on the ROM 304, the RAM 306, or the hard drive 308. Optionally, the scanning interval 603 and/or scan period 601 may be configured by the user, such that, the scanning interval 603 or period 601 may be increased or decreased based on a user input received by the touchscreen 324 or standard keyboard 603. The RF subsystem 330 may continually repeat the scanning interval 603 until the CPU 302 acknowledges receipt of the advertisement notice 605.

The scan period 601 and the advertisement period 602 occur independent and asynchronous with respect to one another, such that the advertisement notices 605 intermittently overlap the scan intervals 603 at 604 and 606. Each period length is predetermined from distinct and separate sources. The scan period 601 is predetermined or configure by the user of the external device 201. Separately, the advertisement period 602 is predetermined by the protocol syntax stored in the memory 408. For example, one of the scan period 601 or the advertisement period 602 may be altered, while, the length of the other period (e.g., advertisement period 602, scan period 601) remains constant.

The scan period 601 has an asynchronous phased relation with respect to the advertisement period 602 in order that a phase interval 615 between beginnings of the scanning intervals 603 and advertisement notices 605 continuously (or intermittently) changes. For example, the scan period 601 may be 4 s having the scanning interval 603 of 1 s, and the advertisement period 602 may be 5 s having the advertisement notice 605 of 1.5 s. The different lengths of the periods 601 and 602 represent the asynchronous phased relationship with respect to each other. The asynchronous phased relationship causes the advertisement notice 605 and the scanning interval 603 to begin at different times thus creating phase intervals 615. The length of the phase interval 615 can be extended and/or shortened by changing the advertisement period 602 of the wireless bridge device 102 or the scan period 601 of the external device 201. Thus, by configuring the advertisement period 602 or the scan period 601, the phase interval 615 may continuously change or be changed intermittently after a set number of cycles. The beginning of the cycle occurs at the transmission of the advertisement notice 605 or the scan interval 603. The phase interval 615 may be controlled by the user changing the scan period 603 of the external device 201 or by the processor circuit 406 changing the advertisement period 602 of the wireless bridge device 102.

For example, the phase interval 615 of the timing diagram 600, is continuously changing after each cycle. The phase interval 615a, measured between the beginning of the advertisement notice 605a and the beginning of the scan interval 603a, may be approximately 1.5 s. The advertisement notice 605a and the scanning interval 603a do not partially or wholly overlap. The phase interval 615b, between the advertisement notice 605b and the scanning interval 603b, may be approximately 750 ms. The phase interval 615c, between the advertisement notice 605c and the scanning interval 603c, may be approximately 250 ms. Accordingly, the length of the phase interval 615 continuously changes each cycle. The changes in the length of the phase interval 615 cooperate such that each cycle or repetition of the scanning interval 603 and the advertisement notice 605 shifts with respect to each other, thereby allowing for partially overlapping events at 604 and 606 to occur. For instance, only the phase intervals 615b-615c are associated with partially overlapping advertisement notices 605b-c and scanning intervals

615b-c. Although the periods 601, 602 are asynchronous, the scanning intervals 603 and the advertisement notices 605 will partially overlap and enable the external device 201 intermittently or after a set number of cycles to receive the advertisement notice 605. The overlaps occur intermittently, in that after a number of cycles the scanning interval 603 and advertisement notice 605 will partially overlap in fewer cycles than the number of cycles. For example, the scanning interval 603 and advertisement notice 605 partially overlap after the fourth and fifth cycle of the scanning interval 603 or the third and fourth cycle of the advertisement notice 605.

Optionally, the wireless bridge device 102 may have a select advertisement mode that decreases the number of cycles needed until the bi-directional communication link 105 is established, by increasing the likelihood of the scanning interval 603 partially overlapping the advertisement notice 605. For example, the select advertisement mode may be activated by the user using the user interface component 416. When the select advertisement mode is activated, the processor circuit 406 may decrease the length of the advertisement period 602, relative to not being in the select advertisement mode, thereby, increasing the number of advertisement notices 605 in a time frame 609. The increased number of advertisement notices 605 increase the number of partial overlaps with the scanning intervals 603, allowing the external device 201 to detect or receive the advertisement notice 605 in a shorter amount of cycles relative to the wireless bridge device 102 not in the select advertisement mode.

Optionally, the wireless bridge device 102 may be programmed and/or configured to disable the RF circuit 420 and/or end or terminate the powered state when a connection request is not received within a predetermined period. The predetermined period may be stored on the memory module 408, defined by the wireless protocol. For example, the wireless bridge device 102 may stop transmitting advertisement notices 605 after the predetermined period, such as five minutes. It should be noted that in other embodiments the predetermined period may be greater than or lesser than five minutes.

Once the external device 201 receives the advertisement notice 605, in the form of a data packet transmitted from the wireless bridge device 102, the CPU 302 analyzes or compares the data packet with the protocol syntax stored on the ROM 304, the RAM 306, or the hard drive 308. The protocol syntax may include the structure of the advertisement notice (e.g., data packet specifications, appropriate number of bits, frequency, or the like) utilized by the wireless protocol. Optionally, the advertisement notice 605 may include a unique code designating the packet as an advertisement. By comparing the protocol syntax with the data packet, the CPU 302 determines whether the received data packet is an advertisement notice 605 using the wireless protocol of the external device 201. If the received data packet is determined not to be an advertisement notice, the external device 201 may continue scanning the advertisement channel. When the CPU 302 determines that the data packet received by the RF circuit 354 is the advertisement notice 605 (having the proper syntax), the CPU 302 outputs a connection request (e.g., within a payload of a data packet) to be transmitted by the RF circuit 354 along the advertisement channel.

The CPU 302 constructs a data packet representing the connection request by adding packet frames to conform to the wireless protocol such as the address of the wireless bridge device 102 and/or external device 201, error detection codes such as CRC, a payload, or the like. The payload may include connection instructions (e.g., frequency of the data channel for the bi-directional communication link 105) from the user intended for the wireless bridge device 102. When the data packet has been formed, the CPU 302 outputs the data packet to the RF subsystem 330 to be transmitted along the advertisement channel that was to the wireless bridge device 102 of the advertisement notice 605. Optionally, the data packet may include connection identification information (e.g., a static identification) corresponding to the IMD 101 to establish the bi-direction communication link 104 as further described below.

The RF circuit 420 receives the data packet from the RF signal received by the antenna 412 via the I/O interface 414. The RF circuit 420 may demodulate the RF signal and output the data packet to the processor circuit 406 via the I/O interface 414. The processor circuit 406 may store the data packet in the memory module 408 for analysis. The processor circuit 406 determines whether the data packet is in response to the advertisement notice 605 by comparing the address information of the data packet with the address transmitted by the wireless bridge device 102 within the advertisement notice 605. If the address information matches, the processor circuit 406 partitions the payload from the data packet and carries out the instruction of the connection request from the payload by comparing the instructions to a stored instruction set on the memory module 408 for the wireless protocol. Optionally, the processor circuit 406 may compare the address information of the external device 201 on the data packet with a permissible links table stored in the memory module 408 to determine whether the wireless bridge device 102 should ignore or partition the payload of the data packet. Once the processor circuit 406 identifies the connection request, the processor circuit 406 may instruct the RF circuit 420 to monitor the data channel identified in the connection request for further instructions from the external device 201, thereby establishing the bi-directional communication link 105.

FIG. 7 illustrates a timing diagram 700 between the external device 201, the wireless bridge device 102, and the IMD 101, according to an embodiment of the present disclosure. The timing diagram 700 may be subdivided into subsections (e.g., 720, 730, 740) corresponding to stages of a bi-directional communication link between the external device 201 and the IMD 101 via the wireless bridge device 102. The subsection 720 corresponds to forming the bi-directional communication link 105, as further described in connection with FIG. 6.

The subsection 730 correspond to a series of data packets 710 and 712 being transmitted from the external device 201 and the wireless bridge device 102 over the bi-directional communication link 105. For example, the external device 201 transmits the data packet 710a along the bi-directional communication link 105. The wireless bridge device 102 receives the data packet 710a and in response transmits the data packet 712a.

Additionally or alternatively, when the bi-directional communication link 105 is established, the bi-directional communication link 105 may be configured to have the external device 201 in a master configuration and the wireless bridge device 102 in a slave configuration as defined by the wireless protocol. While in the master configuration, the external device 201 may have unidirectional control over one or more other devices, such as the wireless bridge device 102. For example, the external device 201 may define a communication interval 732 within the data packet corresponding to the connection request.

The communication interval 732 corresponds to a length of time for the wireless bridge device 102 to respond to a data packet transmitted from the external device 201. The communication interval 732 is defined from an anchor point 734. The anchor point 734 is based on when the external device 201 starts to transmit a data packet 742a to the wireless bridge device 102.

Additional examples of forming a bi-directional communication links is disclosed in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

Returning to FIG. 5, at 504 a second bi-directional communication link (e.g., the bi-directional communication link 104) is established between the wireless bridge device 102 and the IMD 101 concurrently with the first bi-directional communication link (e.g., the bi-directional communication link 105) according to the wireless protocol.

For example, similar to the process described in connection with FIG. 6, the IMD 101 may be configured to enter an advertisement mode. During the advertisement mode, the IMD 101 may broadcast one or more advertisement notices 705 along a dedicated advertisement channel defined by the wireless protocol (e.g., BLE).

The wireless bridge device 102 may receive instructions from the external device 201 corresponding to a data packet 710b. The received instructions may instruct the wireless bridge device 102 to monitor one or more of the dedicated advertisement channels during a scan interval 714 (e.g., similar to the scan intervals 603) for one or more of the advertisement notices 705 transmitted by the IMD 101 to establish the bi-directional communication link 104.

The wireless bridge device 102 may detect at least one of the one or more advertisement notices 705, and establish the bi-directional communication link 104 based on the at least one of the one or more advertisement notices 705. For example, the wireless bridge device 102 receives the advertisement notice 705, in the form of a data packet transmitted from the IMD 101, the processor circuit 406 may analyze or compare the data packet with the protocol syntax stored on the memory module 408. By comparing the protocol syntax with the data packet, the processor circuit 406 determines whether the received data packet is an advertisement notice 705 using the wireless protocol of the IMD 101. If the received data packet is determined not to be an advertisement notice from the IMD 101, the wireless bridge device 102 may continue scanning the advertisement channel. When the processor circuit 406 determines that the data packet received by the RF circuit 420 is the advertisement notice 705 (having the proper syntax), the processor circuit 406 outputs a connection request (e.g., within a payload of a data packet) to be transmitted by the RF circuit 354 along the advertisement channel.

Optionally, the data packet 710b from the external device 201 may include connection identification information of the IMD 101. The connection identification information may correspond to the IMD 101 and is used by the wireless bridge device 102 to establish the bi-directional communication link 104. For example the connection identification information may correspond to a product serial identification number of the IMD 101, which is a unique number assigned to the IMD 101 by a manufacturer of the IMD 101. The connection identification information may be received by the user from the touchscreen 324 or standard keyboard 336. The connection identification information may be used by the wireless bridge device 102 to verify the advertisement notice 705.

For example, the wireless bridge device 102 stores the connection identification information on to the memory module 408 corresponding to a product serial identification number of the IMD 101. The advertisement notice 705 of the IMD 101 may correspond to a data packet with multiple frames defined by the wireless protocol. One of the frames may be an advertising payload which includes the product serial identification number to identify the IMD 101. When the wireless bridge device 102 receives the advertisement notice 705 and determines that the advertisement notice 705 conforms to the protocol syntax, the processor circuit 406 may partition the advertisement payload from the advertisement notice 705. The processor circuit 406 may compare the identification number stored within the advertisement payload with the product serial identification number stored on the memory module 408 received from the external device 201. If the advertiser payload is determined not to match the product serial identification number stored on the memory module 408, the wireless bridge device 102 may continue scanning the advertisement channel (e.g., perform another scan interval 714). When the processor circuit 406 determines that the advertisement payload matches the product serial identification number stored on the memory 408, the processor circuit 406 may output a connection request to be transmitted by the RF circuit 420 along the advertisement channel.

Similarly as described above, the processor circuit 406 constructs a data packet representing the connection request by adding packet frames to conform to the protocol such as the address of the IMD 101 and/or the wireless bridge device 102, error detection codes such as CRC, a payload, or the like. The payload may include connection instructions (e.g., frequency of the data channel for the bi-directional communication link 104). When the data packet has been formed, the processor circuit 406 outputs the data packet to the RF circuit 420 to be transmitted along the advertisement channel that was to the IMD 101 corresponding to the advertisement notice 705. Optionally, the data packet may include identification information corresponding to the external device 201 of the bi-direction communication link 105.

The RF circuit 110 receives the data packet and outputs to the microcontroller 160. The microcontroller 160 may store the data packet in memory 194 for analysis. The microcontroller 160 determines whether the data packet is in response to the advertisement notice 705 by comparing the address information of the data packet with the address transmitted by the IMD 101 within the advertisement notice 705. If the address information matches, the microcontroller 160 partitions the payload from the data packet and carries out the instruction of the connection request from the payload by comparing the instructions to a stored instruction set stored on the memory 194 relating to the wireless protocol. Optionally, the microcontroller 160 may compare the address information of the wireless bridge device 102 and/or the external device 201 on the data packet with a permissible links table stored on memory 194 to determine whether the IMD 101 should ignore or partition the payload of the data packet. Once the microcontroller 150 identifies the connection request, the microcontroller 160 may instruct the RF circuit 110 to monitor the data channel identified in the connection request for further instructions from the wireless bridge device 102, thereby establishing the bi-directional communication link 104.

Additionally or alternatively, when the bi-directional communication link 104 is established, the bi-directional communication link 104 may be configured to have the wireless bridge device 102 in a master configuration and the IMD 101 in a slave configuration as defined by the wireless protocol.

While in the master configuration, the wireless bridge device 102 may have unidirectional control over one or more other devices, such as the IMD 101. For example, the wireless bridge device 102 may define a communication interval 748 within the data packet corresponding to the connection request. The communication interval 748 corresponds to a length of time from an anchor point that the wireless bridge device 102 will receive a data packet from the IMD 101 over the data channel of the bi-directional communication link 104. Optionally, the communication interval 748 may correspond to a time slice within the communication interval 732.

Data passed through the bi-directional communication links 104 and 105 are time sliced with respect to the communication interval 732. For example, the subsection 740 of the timeline correspond to a series of data packets 742, 746, and 744 being transmitted from the external device 201, the wireless bridge device 102, and the IMD over the bi-directional communication links 104 and 105. The series of data packets 742 from the external device 201 may correspond to measurement requests, programming instructions, status updates, and/or the like for the IMD 101. The series of data packets 744 from the IMD 101 may correspond to programmed responses based on the data packets 742 (e.g., measurement requests, programming instructions, status updates). The series of data packets 746 from the wireless bridge device 102 may be re-transmissions of the data packets received from the external device 201 and/or the IMD 101 to the IMD 101 and/or external device 201, respectively.

The communication interval 732 may be subdivided into time slices. The time slices may correspond to when transmission data packets from the wireless bridge device 102 are transmitted over the bi-directional communication links 104 and/or 105, received by the wireless bridge device 102, and/or the like. The time slices enable the exchanges of data packets between the wireless bridge device 102, the IMD 101, and the external device 201 to be within the communication interval maintaining the bi-directional communication links 104 and 105 concurrently and/or simultaneously. Optionally, one of the time slices may correspond to the communication interval 748, allowing transmissions of the series of data packets 744 and 746 to occur within the communication interval 732.

For example, the external device 201 may define the communication interval 732 as 100 ms as a part of the connection request for establishing the bi-directional communication link 105. The wireless bridge device 102 may define the communication interval 748 as 50 ms as a part of the connection request for establishing the bi-directional communication link 104. The external device 201 transmits the data packet 742a to the wireless bridge device 102 over the bi-directional communication link 105. As described above, the data packet 742a may correspond to the anchor point 734 defining a start of the communication interval 732. The RF circuit 420 receives and outputs the data packet 742a to the processor circuit 406. The processor circuit 406 may partition and replace the address information of the data packet 742a corresponding to the wireless bridge device 102 with the address information of the IMD 101, thereby constructing the data packet 746a. It should be noted in various embodiments, the processor circuit 406 does not partition and/or process a payload of the data packet 742a.

The processor circuit 406 may output the data packet 746a to the RF circuit 420 via the I/O interface 414 to be transmitted along the data channel of the bi-directional communication link 104. As described above, the data packet 746a may correspond to the anchor point defining the communication interval 748.

The RF circuit 110 receives the data packet and outputs the data packet 746a to the microcontroller 160. The microcontroller 160 may partition the payload from the data packet 746a and carries out the instruction of the external device 201 from the payload by comparing the instructions to a stored instruction and/or command set on the memory 194 for the wireless protocol.

The microcontroller 160 constructs a data packet 744a with a payload corresponding to the instructions of the external device 201 conforming to the wireless protocol of the bi-directional communication link 104. The microcontroller 160 transmits the data packet 744a via the RF circuit 110 within the communication interval 748.

The RF circuit 420 receives and outputs the data packet 744a to the processor circuit 406. The processor circuit 406 may partition and replace the address information of the data packet 744a that corresponds to the wireless bridge device 102 with the address information of the external device 102, constructing the data packet 746b. The processor circuit 406 outputs the data packet 746b to the RF circuit 420 via the I/O interface 414 to be transmitted along the data channel of the bi-directional communication link 105.

The external device 201 receives the data packet 746b via the RF circuit 354 within the communication interval 732. The RF circuit 354 outputs the data packet 746a to the CPU 302 and/or 352. The CPU 302 and/or 352 may partition the payload from the data packet 746b and carries out the instruction of the external device 201 from the payload by comparing the instructions to a stored instruction and/or command set on the ROM 304, RAM 306, and/or hard drive 308 for the wireless protocol.

Optionally, the data packet 742a received by the wireless bridge device 102 is over a first dedicated data channel of the bi-directional communication link 105, and the data packet 746a is transmitted from the wireless bridge device 102 to the IMD 101 over a second dedicated data channel of the bi-directional communication link 104.

Optionally, the length of the communication interval 732 may be based on a command action from the user and/or within the payload of the series of data packets 742. For example, the user may instruct the external device 201 to transmit a command action to the IMD 101, such as program the IMD 101, receive measurements from the IMD 101, request a status update of the IMD 101, and/or the like. Each of the command actions may correspond to differing lengths of data packets being transmitted from the IMD 101 and/or the external device 201. For example, the series of data packets 742 from the external device 201 may have larger payloads relative to the series of data packets 744 from the IMD 101. In another example, the series of data packets 744 from the IMD 101 may have larger payloads relative to the series of data packets 742. In various embodiments, the payloads for each The length of the communication interval 732 may vary depending on the size of the payloads from the external device 201 and/or the IMD 101 based on the command action. For example, a length of the communication interval 732 may be smaller when the user instructs the external device 201 to program the IMD 101 relative to communication intervals corresponding to command actions of measurement requests from the IMD 101.

Returning to FIG. 5, at 506 a data packet (e.g., 710, 742) from the external device 201 is received at the wireless bridge 102 during a communication interval (e.g., 732). For example, the wireless bridge device 102 may receive the data packet 742*a* from the external device 201 over a first dedicated data channel of the bi-directional communication link 105.

At 508, the data packet (e.g., 746) from the wireless bridge device 102 is transmitted to the IMD 101 during the communication interval (e.g., 732). For example, the wireless bridge device 102 may transmit the data packet 746*a* to the IMD 101 over a second dedicated data channel of the bi-directional communication link 104 during the communication interval 732.

At 510, a second data packet (e.g., 744) from the IMD 101 is received at the wireless bridge device 102 during the communication interval (e.g., 732). For example, the wireless bridge device 102 may receive the data packet 744*a* from the IMD 101 over the second dedicated data channel of the bi-directional communication link 104 during the communication interval 732.

At 512, the second data packet (e.g., 746) for the wireless bridge device 102 is transmitted to the external device 201 during the communication interval (e.g., 732). For example, the wireless bridge device 102 may transmit the data packet 746*b* to the external device 201 over the first dedicated data channel of the bi-directional communication link 105 during the communication interval 732.

Various embodiments described herein may implement the method 800 illustrated in FIG. 8. Beginning at 802, the wireless bridge device 102 may be activated. For example, the wireless bridge device 102 may enter into an advertisement mode such that the wireless bridge device 102 broadcasts one or more advertisement notices 605 along one or more dedicated advertisement channels defined by the wireless protocol.

At 804, the wireless bridge device 102 may continually broadcast the one or more advertisement notices 605 until a connection request is received by the external device 201 (master 0).

At 806, when the connection request is received by the wireless bridge device 102, the wireless bridge device 102 is connected to the external device 201 over the bi-directional communication link 105. The bi-directional communication link 105 may be configured with the external device 201 as a master device, such as master 0, and the wireless bridge device 102 as a slave device, such as slave 0.

At 808, the wireless bridge device 102 may scan one or more advertisement channels for the one or more advertisement notices 705 transmitted by the IMD 101.

Optionally, when the wireless device 102 is connected to the external device 201, the external device 201 may transmit connection information (e.g. a serial number) from the IMD 101. The connection information may be used by the wireless bridge device 102 to establish a connection with the IMD 101.

Additionally or alternatively, the wireless bridge device 102 may scan one or more advertisement channels for one or more advertisement notices that originate from one or more peripheral devices, respectively. The one or more peripheral devices may correspond to one or more IMDs, medical devices, auxiliary devices, imaging system and/or the like that are transmitting advertisement notices based on the wireless protocol. For example, the RF circuit 420 may continually shift the scan interval 603 between select frequencies that correspond to the one or more advertisement channels of the wireless protocol. When the wireless bridge device 102 receives the one or more advertisement notices (e.g., 705), the processor circuit 406 may store the one or more advertisement notices on the memory module 408.

The wireless bridge device 102 may generate a list of select peripherals from the one or more peripheral devices detected. The select peripherals may correspond to one or more IMDs and/or other medical devices the wireless bridge device 102 may form a bi-directional communication link. For example, the memory module 408 may include a list of manufacturers, product serial numbers, and/or the like of identification characteristics of the select peripheral devices. The processor circuit 406 may compare the identification characteristics with the identification characteristics of the detected peripheral devices based from the one or more advertisement notices.

For example, the processor circuit 406 may partition the payload from the one or more advertisement notices stored on the memory module 408. The processor circuit 406 may compare the one or more partitioned payloads with the protocol syntax on the memory module 408 to determine identification information, such as manufacturer or product serial numbers of the corresponding peripheral. The processor circuit 406 determines which detected peripheral is a select peripheral by comparing the identification information stored on the memory module 408. If the identification information of the detected peripheral matches the identification information stored on the memory module 408, the processor circuit 406 may include the detected peripheral to the list.

The wireless bridge device 102 may transmit the list to the external device 201 over the bi-directional communication link 105. The list may be displayed on the display 322 of the external device 201. The user may select from the displayed list using the touchscreen 324 or standard keyboard 326 one of the select peripheral devices, such as the IMD 101, to be connected with the wireless bridge device 102 over the bi-directional communication link 104. When the select peripheral device is selected, the external device 201 may transmit instructions for the wireless bridge device 102 to establish the bi-directional communication link 104 with the selected peripheral device.

At 810, the wireless bridge device 102 establishes the bi-directional communication link 104 with the IMD 101. For example, the wireless bridge device 102 may transmit a connection request to the IMD 101 in response the one or more advertisement notices 705. The bi-directional communication link 104 may be configured with the wireless bridge device 102 as a master device, and the IMD 101 as a slave device, such as slave 1.

At 812, the wireless bridge device 102 passes or transmits data packets (e.g., the data packets 746 corresponding to the data packets 742) received from the external device 201 (master 0) to the IMD 101 (slave 1) and data packets (e.g., the data packets 746 corresponding to the data packets 744) received from the IMD 101 (slave 1) to the external device 201 (master 0). The wireless bridge device 102 may continually transmit the data packets 746 until a termination request 752 is received from the external device 201.

At 814, the wireless bridge device 102 closes the upper stream link (e.g., the bi-directional communication link 105). The wireless bridge device 102 receives the termination request 752 from the external device 201. For example, the termination request 752 may be included in a data packet received by the RF circuit 420. The RF circuit 420 may output the data packet to the processor circuit 406. The processor circuit 406 may verify the termination request 752 by comparing particular frames of the data packet (e.g., a header of the data packet), the payload of the data packet, and/or the like. When the processor circuit 406 verifies the termination request 752, the processor circuit 406 may terminate or close the bi-directional communication link 105. For example, after the bi-directional communication link 105 is terminated the processor circuit 406 may ignore data packets having address information corresponding to the external device 201. Optionally, the processor circuit 406 may instruct the RF circuit 420 to transmit a confirmation data packet 754 to the external device 201.

At 816, the wireless bridge device 102 closes the downstream link (e.g., the bi-directional communication link 104). The wireless bridge may transmit the termination request 756 to the IMD 101. For example, the wireless bridge device 102 may retransmit the data packet of the termination request 752 to the IMD 101. The RF circuit 110 may output the data packet to the microcontroller 160. The microcontroller 160 may verify the termination request 756 by comparing particular frames of the data packet (e.g., a header of the data packet), the payload of the data packet, and/or the like. When the microcontroller 160 verifies the termination request 756, the microcontroller 160 may terminate or close the bi-directional communication link 104. For example, after the bi-directional communication link 104 is terminated, the microcontroller 160 may or data packets having address information corresponding to the wireless bridge device 102. Optionally, the microcontroller 160 may instruct the RF circuit 110 to transmit a confirmation data packet 758 to the wireless bridge device 102.

Additionally or alternatively, when the bi-directional communication links 104 and 105 have been terminated or closed, the wireless bridge device may continually broadcast the one or more advertisement notices 605 over one or more advertisement channels (e.g., 804).

Additionally or alternatively, when the bi-directional communication link 104 has been terminated or closed, the IMD 101 may continually broadcast the one or more advertisement notices 705 over one or more advertisement channels.

Figure 9:
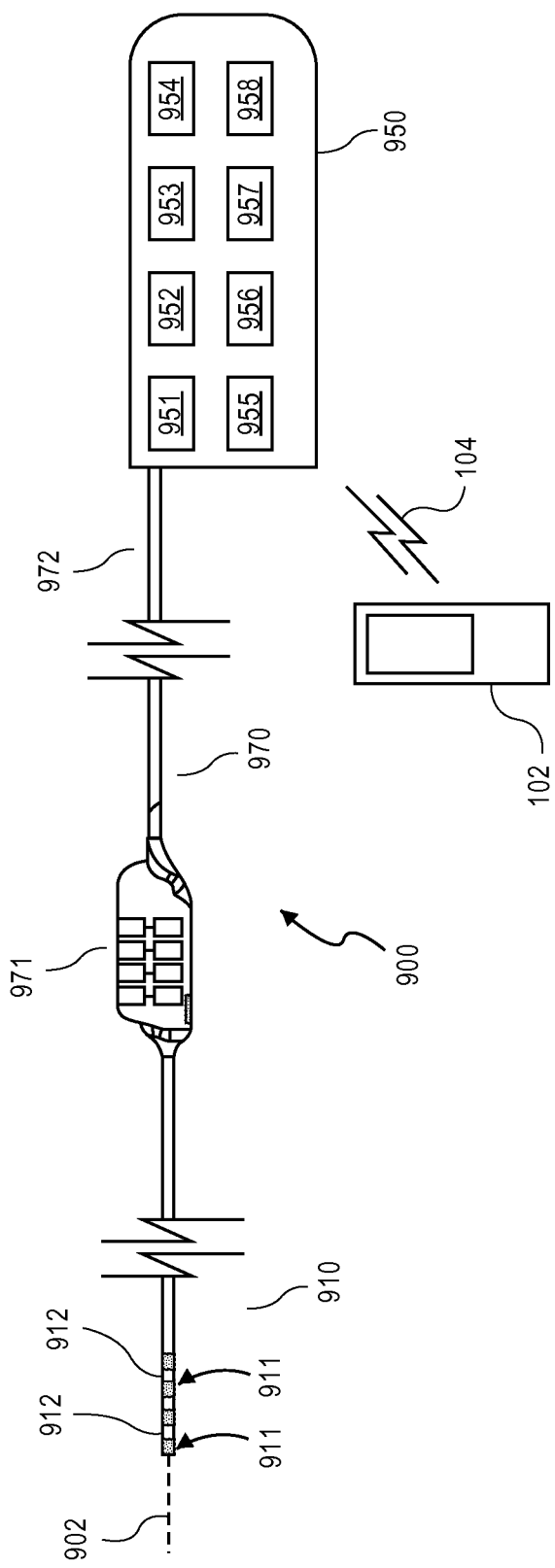
FIG. 9 illustrates a block diagram of exemplary internal components of an implantable medical device, according to an embodiment of the present disclosure.

FIG. 9 illustrates a block diagram of exemplary internal components of the IMD 900, in accordance with an embodiment. For example, the IMD 900 may be a neurostimulator adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The IMD 900 may include an implantable pulse generator (IPG) 950 that is adapted to generate electrical pulses applied to the tissue of a patient. Additionally or alternatively, the IPG 950 may be an external neuro pulse generator. The IPG 950 typically comprises a metallic housing that encloses a controller 951, pulse generating circuitry 952, a charging coil 953, a battery 954, RF circuit 955, battery charging circuitry 956, switching circuitry 957, memory 958, and the like.

The controller 951 (also referred to herein as a processor module or unit) typically includes a microprocessor, or equivalent control circuitry, designed specifically for controlling the components of the IPG 950 and may further include RAM or ROM memory, logic and timing circuitry, state machine circuitry, and I/O circuitry. Typically, the controller 951 includes the ability to process or monitor input signals (data) as controlled by program code stored in memory. The details of the design and operation of the controller 951 are not critical to the invention. Rather, any suitable controller 951 may be used that carries out the functions described herein.

The IPG 950 may comprise a separate or an attached extension component 970. If the extension component 970 is a separate component, the extension component 970 may connect with a "header" portion of the IPG 950 as is known in the art. If the extension component 970 is integrated with the IPG 950, internal electrical connections may be made through respective conductive components. Within the IPG 950, electrical pulses are generated by the pulse generating circuitry 952 and are provided to the switching circuitry 957. The switching circuitry 957 connects to outputs of the IPG 950. Electrical connectors (e.g., "Bal-Seal" connectors) within the connector portion 971 of the extension component 970 or within the IPG header may be employed to conduct various stimulation pulses. The terminals of one or more leads 910 are inserted within connector portion 971 or within the IPG header for electrical connection with respective connectors. Thereby, the pulses originating from the IPG 950 are provided to the leads 910. The pulses are then conducted through the conductors of the lead 910 and applied to tissue of a patient via stimulation electrodes 911 that may be coupled to blocking capacitors. Any suitable known or later developed design may be employed for connector portion 971.

The stimulation electrodes 911 may be positioned along a horizontal axis 902 of the lead 910, and are angularly positioned about the horizontal axis 802 so the stimulation electrodes 911 do not overlap. The stimulation electrodes 911 may be in the shape of a ring such that each stimulation electrode 911 continuously covers the circumference of the exterior surface of the lead 910. Each of the stimulation electrodes 911 are separated by non-conducting rings 912, which electrically isolate each stimulation electrode 911 from an adjacent stimulation electrode 911. The non-conducting rings 912 may include one or more insulative materials and/or biocompatible materials to allow the lead 910 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 911 may be configured to emit the pulses in an outward radial direction proximate to or within a stimulation target. Additionally or alternatively, the stimulation electrodes 911 may be in the shape of a split or non-continuous ring such that the pulse may be directed in an outward radial direction adjacent to the stimulation electrodes 911. Examples of a fabrication process of the stimulation electrodes 911 is disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is expressly incorporated herein by reference.

It should be noted the stimulation electrodes 911 may be in various other formations, for example, in a planar formation on a paddle structure as disclosed in U.S. Provisional Application No. 61/791,288, entitled, "PADDLE LEADS FOR NEUROSTIMULATION AND METHOD OF DELIVERING THE SAME," which is expressly incorporated herein by reference.

The lead 910 may comprise a lead body 972 of insulative material about a plurality of conductors within the material that extend from a proximal end of lead 910, proximate to the IPG 950, to its distal end. The conductors electrically couple a plurality of the stimulation electrodes 911 to a plurality of terminals (not shown) of the lead 910. The terminals are adapted to receive electrical pulses and the stimulation electrodes 911 are adapted to apply the pulses to the stimulation target of the patient. Also, sensing of physiological signals may occur through the stimulation electrodes 911, the conductors, and the terminals. It should be noted that although the lead 910 is depicted with four stimulation electrodes 911, the lead 910 may include any suitable number of stimulation electrodes 911 (e.g., less than four, more than four) as well as terminals, and internal conductors. Additionally or alternatively, various sensors (e.g., a position detector, a radiopaque fiducial) may be located near the distal end of the lead 910 and electrically coupled to terminals through conductors within the lead body 972.

For implementation of the components within the IPG 950, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 956) of an IPG 950 using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 952) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 950. Different pulses on different stimulation electrodes 911 may be generated using a single set of the pulse generating circuitry 952 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 911 as is also known in the art. Various sets of parameters may define the pulse characteristics and pulse timing for the pulses applied to the various stimulation electrodes 911 as is known in the art. Although constant current pulse generating circuitry is contemplated for some embodiments, any other suitable type of pulse generating circuitry may be employed such as constant voltage pulse generating circuitry.

The stimulation parameters (e.g., amplitude, frequency, type of stimulation waveform) and other operating parameters of the IMD 900 may be non-invasively programmed into the memory 958 through the RF circuit 955 in bi-directional wireless communication link 104. For example, the external device 201 may permit the user to move electrical stimulation along and/or across one or more of the lead(s) 910 using different stimulation electrode 911 combinations by communicating to the IMD 900 via the wireless bridge device 102, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. The controller 951 controls the RF circuit 955 and receives data/transmissions from the RF circuit 955. The RF circuit 955 further allows status information relating to the operation of IMD 900 (as contained in the controller 951 or memory 958) to be sent to via the bi-directional communication link 104.

The controller 951 may support a particular wireless communication protocol while communicating with the wireless bridge device 102 and/or the external device 201, such as Bluetooth low energy, Bluetooth, ZigBee, Medical Implant Communication Service ("MICS"), or the like. Protocol firmware may be stored in memory 958, which is accessed by the controller 951. The protocol firmware provides the wireless protocol syntax for the controller 951 to assemble data packets, establish communication links 104, and partition data received from the bi-directional communication link 104.

The memory 958 may also contain a pre-defined algorithm that generates a passkey. The passkey may be used to initiate a bonding procedure between the IMD 900 and the external device 201 to establish a secured bi-directional communication session over the bi-directional communication link 104. The passkey may be generated based on a dynamic seed and/or a static identification received by the RF circuit 955 through the bi-directional communication link 104 from the wireless bridge device 102 and inputted into the pre-defined algorithm. Optionally, the dynamic seed may be a random number generated by the controller 951, based on the local system clock of the IMD 900, or the like that is transmitted by the RF circuit 955 to the external device. Additionally or alternatively, the static identification may be stored on the memory 958 representing a product serial identification number of the IMD 900, which is a unique number assigned to the IMD 900 by a manufacturer of the IMD 900. Optionally, the static identification may be a pre-determined number stored on the memory 958 set by a user.

The controller 951, the processor circuit 406, the microcontroller 160, and CPUs 302 and 352 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 951, the processor circuit 406, the microcontroller 160, and CPUs 302 and 352 represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 951, the processor circuit 406, the microcontroller 160, and CPUs 302 and 352 may execute a set of instructions that are stored in one or more storage elements, in order to process data. The storage elements may also store data or other information as desired or needed. The storage element may be in the form of an information source or a physical memory element within the controller 951, the processor circuit 406, the microcontroller 160, and CPUs 302 and 352. The set of instructions may include various commands that instruct the controller 951, the processor circuit 406, the microcontroller 160, and CPUs 302 and 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for bridging a bi-directional communication link between an external device and an implantable medical device (IMD), the method comprising:
   establishing a first bi-directional communication link between an external device and a wireless bridge device according to a wireless protocol;
   establishing a second bi-directional communication link between the wireless bridge device and an IMD concurrently with the first bi-directional communication link according to the wireless protocol, wherein the wireless protocol establishes a communication link between the wireless bridge device and the IMD according to at least one of a Bluetooth protocol, a Bluetooth low energy protocol, or a ZigBee protocol;
   receiving a data packet from the external device at the wireless bridge device, wherein the data packet is received during a communication interval; and
   transmitting the data packet from the wireless bridge device to the IMD during the communication interval.

2. The method of claim 1, further comprising:
   receiving a second data packet from the IMD at the wireless bridge device during the communication interval; and
   transmitting the second data packet from the wireless bridge device to the external device during the communication interval.

3. The method of claim 1, wherein the communication interval is subdivided into time slices, at least one of the time slices corresponding to the transmitting operation of the data packet from the wireless bridge device to the IMD.

4. The method of claim 1, wherein a length of the communication interval is based on a command action, wherein the command action corresponds to at least one of program the IMD, receive measurements from the IMD, or request a status update of the IMD.

5. The method of claim 1, further comprising:
   receiving connection identification information from the external device over the first bi-directional communication link, wherein the connection identification information corresponds to the IMD and is used to establish the second bi-directional communication link.

6. The method of claim 1, further comprising:
   configuring the wireless bridge device to enter an advertisement mode, wherein during the advertisement mode the wireless bridge device broadcasts one or more advertisement notices along a dedicated advertisement channel defined by the wireless protocol;
   detecting at least one of the one or more advertisement notices at the external device, wherein the first bi-directional communication link is established based on the at least one of the one or more advertisement notices.

7. The method of claim 1, further comprising:
   configuring the first bi-directional communication link to have the external device in a master configuration and the wireless bridge device in a slave configuration as defined by the wireless protocol; and
   configuring the second bi-directional communication link to have the wireless bridge device in a master configuration and the IMD in a slave configuration as defined by the wireless protocol.

8. A method for bridging a bi-directional communication link between an external device and an implantable medical device (IMD), the method comprising:
   establishing a first bi-directional communication link between an external device and a wireless bridge device according to a wireless protocol;
   establishing a second bi-directional communication link between the wireless bridge device and an IMD concurrently with the first bi-directional communication link according to the wireless protocol;
   scanning one or more advertisement channels by the wireless bridge device for one or more advertisement notices that originate from one or more peripheral devices, respectively; and generating a list of select peripherals from the one or more peripheral devices, wherein at least one of the select peripherals is the IMD.

9. The method of claim 8, further comprising:
transmitting the list from the wireless bridge to the external device; and
selecting the IMD from the list at the external device.

10. The method of claim 1, wherein the wireless bridge device includes a Bluetooth Low Energy System on Chip.

11. The method of claim 1, wherein the wireless protocol establishes a communication link between the wireless bridge device and the external device according to at least one of a Bluetooth protocol, a Bluetooth low energy protocol, or a ZigBee protocol.

12. The method of claim 1, further comprising:
configuring the IMD to enter an advertisement mode, wherein during the advertisement mode the IMD broadcasts one or more advertisement notices along a dedicated advertisement channel defined by the wireless protocol;
detecting at least one of the one or more advertisement notices at the wireless bridge device, wherein the second bi-directional communication link is established based on the at least one of the one or more advertisement notices.

13. The method of claim 1, further comprising:
receiving a termination request from the external device at the wireless bridge device; and
transmitting the termination request to the IMD from the wireless bridge device.

14. A wireless bridge device for bridging a bi-directional communication link between an external device and an implantable medical device (IMD) comprising:
a housing;
at least one antenna; and
a System on Chip (SoC) within the housing electrically coupled to the at least one antenna, the SoC includes one or more processors and is configured to:
establish a first bi-directional communication link with an external device according to a wireless protocol,
establish a second bi-directional communication link with an IMD concurrently with the first bi-directional communication link according to the wireless protocol, wherein the second bi-directional communication link with the IMD uses at least one of a Bluetooth protocol, a Bluetooth low energy protocol, or a ZigBee protocol,
receive a data packet from the external device via the at least one antenna during a communication interval, and
transmit the data packet to the IMD via the at least one antenna during the communication interval.

15. The wireless bridge device of claim 14, wherein the SoC is further configured to:
receive a second data packet from the IMD via the at least one antenna during the communication interval; and
transmit the second data packet to the external device via the at least one antenna during the communication interval.

16. The wireless bridge device of claim 14, wherein the communication interval is subdivided into time slices, at least one of the time slices corresponding to the transmitting operation of the data packet from the wireless bridge device to the IMD.

17. The wireless bridge device of claim 14, wherein the SoC is further configured to:
receive connection identification information from the external device over the first bi-directional communication link, wherein the connection identification information corresponds to the IMD and is used to establish the second bi-directional communication link.

18. The wireless bridge device of claim 14, wherein the SoC is further configured to:
enter an advertisement mode, wherein during the advertisement mode the at least one antenna broadcasts one or more advertisement notices along a dedicated advertisement channel defined by the wireless protocol; and
detect a connection request from the external device during the advertisement mode, wherein the first bi-directional communication link is established based on the detection request.

19. The wireless bridge device of claim 14, wherein the SoC is further configured to:
operate in a slave configuration with respect to the external device corresponding to the first bi-directional communication link as defined by the wireless protocol; and
operate in a master configuring with respect to the IMD corresponding to the second bi-directional communication link as defined by the wireless protocol.

20. The wireless bridge device of claim 14, wherein the SoC is further configured to:
scan one or more advertisement channels for one or more advertisement notices that originate from one or more peripheral devices; and
generate a list of select peripherals from the one or more peripheral devices, wherein at least one of the select peripherals is the IMD.

* * * * *